(12) United States Patent
Cardozo et al.

(10) Patent No.: US 12,246,012 B2
(45) Date of Patent: Mar. 11, 2025

(54) METHOD FOR TREATING NERVOUS SYSTEM INJURIES USING BOLDINE AND DERIVATIVES THEREOF

(71) Applicants: United States Government as Represented by the Department of Veterans Affairs, Washington, DC (US); Juan C. Saez, Vina Del Mar (CL)

(72) Inventors: Christopher Cardozo, Bronx, NY (US); Carlos A. Toro Chacon, Bronx, NY (US); Zachary Graham, Birmingham, AL (US); Wei Zhao, Bronx, NY (US); Juan C. Saez, Vina del Mar (CL)

(73) Assignees: United States Government as represented by the Department of Veterans Affairs, Washington, DC (US); Juan Saez, Vina Del Mar (CL)

( * ) Notice: Subject to any disclaimer, the term of this patent is extended or adjusted under 35 U.S.C. 154(b) by 77 days.

(21) Appl. No.: 18/125,612

(22) Filed: Mar. 23, 2023

(65) Prior Publication Data

US 2023/0233548 A1 Jul. 27, 2023

Related U.S. Application Data

(62) Division of application No. 17/170,821, filed on Feb. 8, 2021, now Pat. No. 11,707,459.

(60) Provisional application No. 63/043,572, filed on Jun. 24, 2020, provisional application No. 62/971,757, filed on Feb. 7, 2020.

(51) Int. Cl.
*A61K 31/47* (2006.01)
*A61P 25/00* (2006.01)

(52) U.S. Cl.
CPC .............. *A61K 31/47* (2013.01); *A61P 25/00* (2018.01)

(58) Field of Classification Search
None
See application file for complete search history.

(56) References Cited

U.S. PATENT DOCUMENTS

| 8,188,065 B2 | 5/2012 | Ellies et al. |
| 2014/0023653 A1 | 1/2014 | Ellies et al. |

FOREIGN PATENT DOCUMENTS

| WO | WO 02-077017 A2 | 10/2002 | |
| WO | WO 2010-026487 | 3/2010 | |
| WO | WO-2011127586 A1 * | 10/2011 | ........... A61K 31/198 |
| WO | PCT/US21/16943 | 2/2021 | |

OTHER PUBLICATIONS

Remandet et al, Neurobehavioral Toxicology and Teratology, 5(3), 305-8 (Year: 1983).*
Ahuja, C. S., S. Nori, L. Tetreault, J. Wilson, B. Kwon, J. Harrop, D. Choi and M. G. Fehlings (2017). "Traumatic Spinal Cord Injury-Repair and Regeneration." Neurosurgery 80(3S): S9-S22.
Ataoglu, E., T. Tiftik, M. Kara, H. Tunc, M. Ersoz and S. Akkus (2013). "Effects of chronic pain on quality of life and depression in patients with spinal cord injury." Spinal Cord 51(1): 23-26.
Austin, P. J. and G. Moalem-Taylor (2010). "The neuro-immune balance in neuropathic pain: involvement of inflammatory immune cells, immune-like glial cells and cytokines." J Neuroimmunol 229(1-2): 26-50.
Basso, D. M., L. C. Fisher, A. J. Anderson, L. B. Jakeman, D. M. McTigue and P. G. Popovich (2006). "Basso Mouse Scale for locomotion detects differences in recovery after spinal cord injury in five common mouse strains." J Neurotrauma 23(5): 635-659.
Bazargani, N., and D. Attwell. 2016. 'Astrocyte calcium signaling: the third wave', Nat Neurosci, 19: 182-9.
Bennett, M. V., J. E. Contreras, F. F. Bukauskas and J. C. Saez (2003). "New roles for astrocytes: gap junction hemichannels have something to communicate." Trends Neurosci 26(11): 610-617.
Cafferty, W. B., P. Duffy, E. Huebner and S. M. Strittmatter (2010). "MAG and OMgp synergize with Nogo-A to restrict axonal growth and neurological recovery after spinal cord trauma." J Neurosci 30(20): 6825-6837.
Castany, S., G. Gris, J. M. Vela, E. Verdu and P. Boadas-Vaello (2018). "Critical role of sigma-1 receptors in central neuropathic pain-related behaviours after mild spinal cord injury in mice." Sci Rep 8(1): 3873.
Cea, L. A., B. A. Cisterna, C. Puebla, M. Frank, X. F. Figueroa, C. Cardozo, K. Willecke, R. Latorre and J. C. Saez (2013). "De novo expression of connexin hemichannels in denervated fast skeletal muscles leads to atrophy." Proc Natl Acad Sci U S A 110(40): 16229-16234.
Chen, G., C. K. Park, R. G. Xie, T. Berta, M. Nedergaard, and R. R. Ji. 2014. 'Connexin-43 induces chemokine release from spinal cord astrocytes to maintain late-phase neuropathic pain in mice', Brain, 137: 2193-209.
Chever, 0., C. Y. Lee, and N. Rouach. 2014. 'Astroglial connexin43 hemichannels tune basal excitatory synaptic transmission', J Neurosci, 34: 11228-32.
Cisterna, B. A., A. A. Vargas, C. Puebla, and J. C. Saez. 2016. 'Connexin hemichannels explain the ionic imbalance and lead to atrophy in denervated skeletal muscles', Biochim Biophys Acta, 1862: 2168-76.
Colleoni, M. and P. Sacerdote (2010). "Murine models of human neuropathic pain." Rinchim Biophys Acta 1802(10): 924-933.
Contreras, J. E., J. C. Saez, F. F. Bukauskas, and M. V. Bennett. 2003. 'Gating and regulation of connexin 43 (Cx43) hemichannels', Proc Natl Acad Sci U S A, 100: 11388-93.

(Continued)

*Primary Examiner* — Zinna Northington Davis
(74) *Attorney, Agent, or Firm* — Ballard Spahr LLP

(57) ABSTRACT

Provided are methods of treating an injury to the nervous system in a subject comprising administering to the subject an effective amount of boldine, a boldine analog, or a pharmaceutically-acceptable salt thereof. Also provided are methods of improving voluntary muscle control and methods of treating neuropathic pain in a subject having an injury to the nervous system. This abstract is intended as a scanning tool for purposes of searching in the particular art and is not intended to be limiting of the present disclosure.

8 Claims, 9 Drawing Sheets

(56) References Cited

OTHER PUBLICATIONS

Courtine, G., B. Song, R. R. Roy, H. Zhong, J. E. Herrmann, Y. Ao, J. Qi, V. R. Edgerton, and M. V. Sofroniew. 2008. 'Recovery of supraspinal control of stepping via indirect propriospinal relay connections after spinal cord injury', Nat Med, 14: 69-74.

Dallerac, G., 0. Chever, and N. Rouach. 2013. 'How do astrocytes shape synaptic transmission? Insights from electrophysiology', Front Cell Neurosci, 7: 159.

Deuis, J. R., L. S. Dvorakova and I. Vetter (2017). "Methods Used to Evaluate Pain Behaviors in Rodents" Front Mol Neurosci 10: 284.

Evans, W. H., E. De Vuyst, and L. Leybaert. 2006. 'The gap junction cellular internet: connexin hemichannels enter the signalling limelight', Biochem J, 397: 1-14.

Ezan, P., P. Andre, S. Cisternino, B. Saubamea, A. C. Boulay, S. Doutremer, M. A. Thomas, N. Quenech'du, C. Giaume, and M. Cohen-Salmon. 2012. 'Deletion of astroglial connexins weakens the blood-brain barrier', J Cereb Blood Flow Metab, 32: 1457-67.

Fehlings, M. G., and G. W. Hawryluk. 2010. 'Scarring after spinal cord injury', J Neurosurg Spine, 13: 165-7; discussion 67-8.

Fernandez, J., P. Lagos, P. Rivera, and E. Zamorano-Ponce. 2009. 'Effect of boldo (*Peumus boldus* Molina) infusion on lipoperoxidation induced by cisplatin in mice liver', Phytother Res, 23: 1024-7.

Filipp, M. E., B. J. Travis, S. S. Henry, E. C. Idzikowski, S. A. Magnuson, M. Y. Loh, D. J. Hellenbrand, and A. S. Hanna. 2019. 'Differences in neuroplasticity after spinal cord injury in varying animal models and humans', Neural Regen Res, 14: 7-19.

Fitch, M. T., and J. Silver. 2008. 'CNS injury, glial scars, and inflammation: Inhibitory extracellular matrices and regeneration failure', Exp Neurol, 209: 294-301.

Giaume, C., L. Leybaert, C. C. Naus, and J. C. Saez. 2013. 'Connexin and pannexin hemichannels in brain glial cells: properties, pharmacology, and roles', Front Pharmacol, 4: 88.

Giaume, C., and X. Liu. 2012. 'From a glial syncytium to a more restricted and specific glial networking', J Physiol Paris, 106: 34-9.

Giaume, C., and K. D. McCarthy. 1996. 'Control of gap-junctional communication in astrocytic networks', Trends Neurosci, 19: 319-25.

Giaume, C., A. Tabernero, and J. M. Medina. 1997. 'Metabolic trafficking through astrocytic gap junctions', Glia, 21: 114-23.

Gonzales, C., M. M. Zaleska, D. R. Riddell, K. P. Atchison, A. Robshaw, H. Zhou and S. J. Sukoff Rizzo (2014). "Alternative method of oral administration by peanut butter pellet formulation results in target engagement of BACE1 and attenuation of gavage-induced stress responses in mice." Pharmacol Biochem Behav 126: 28-35.

Goralski, C. T., et al. "Isoquinoline Alkaloids 2. Preparation of d,I-Glaucine 1.5 Phosphate from d, I-Laudanosoline Hydrobromide" Organic Process Research & Development (1997) 1(4) 273-279.

Harris, A. L. (2007). "Connexin channel permeability to cytoplasmic molecules." Prog Biophys Mol Biol 94(1-2): 120-143.

Henneberger, C., T. Papouin, S. H. Oliet, and D. A. Rusakov. 2010. 'Long-term potentiation depends on release of D-serine from astrocytes', Nature, 463: 232-6.

Henton, D.R., et al Journal of Labelled Compounds and Radiopharmaceuticals (1989), 27(3), 297-307.

Hulsebosch, C. E., B. C. Hains, E. D. Crown and S. M. Carlton (2009). "Mechanisms of chronic central neuropathic pain after spinal cord injury." Brain Res Rev 60(1): 202-213.

Hulsebosch, C. E., G. Y. Xu, J. R. Perez-Polo, K. N. Westlund, C. P. Taylor and D. J. McAdoo (2000). "Rodent model of chronic central pain after spinal cord contusion injury and effects of gabapentin." J Neurotrauma 17(12): 1205-1217.

Huang, C., X. Han, X. Li, E. Lam, W. Peng, N. Lou, A. Torres, M. Yang, J. M. Garre, G. F. Tian, M. V. Bennett, M. Nedergaard, and T. Takano. 2012. 'Critical role of connexin 43 in secondary expansion of traumatic spinal cord injury', J Neurosci, 32: 3333-8.

Jensen, M. P., M. J. Chodroff and R. H. Dworkin (2007). "The impact of neuropathic pain on health- related quality of life: review and implications." Neurology 68(15): 1178-1182.

Ji, R. R., Z. Z. Xu and Y. J. Gao (2014). "Emerging targets in neuroinflammation-driven chronic pain" Nat Rev Drug Discov 13(7): 533-548.

Kim, D., S. Lee and S. J. Lee (2009). "Toll-like receptors in peripheral nerve injury and neuropathic pain" Curr Top Microbiol Immunol 336: 169-186.

Leal-Filho, M. B. 2011. 'Spinal cord injury: From inflammation to glial scar', Surg Neurol Int, 2: 112.

Lee, I. H., E. Lindqvist, 0. Kiehn, J. Widenfalk, and L. Olson. 2005. 'Glial and neuronal connexin expression patterns in the rat spinal cord during development and following injury', J Comp Neural, 489: 1-10.

Maeda, S., S. Nakagawa, M. Suga, E. Yamashita, A. Oshima, Y. Fujiyoshi and T. Tsukihara (2009). "Structure of the connexin 26 gap junction channel at 3.5 A resolution." Nature 458(7238): 597-602.

Mao, Y., T. Nguyen, R. S. Tonkin, J. G. Lees, C. Warren, S. J. O'Carroll, L. F. B. Nicholson, C. R. Green, G. Moalem-Taylor and C. A. Gorrie (2017). "Characterisation of Peptide5 systemic administration for treating traumatic spinal cord injured rats" Exp Brain Res 235(10): 3033-3048.

Mao, Y., R. S. Tonkin, T. Nguyen, S. J. O'Carroll, L. F. Nicholson, C. R. Green, G. Moalem-Taylor and C. A. Gorrie (2017). "Systemic Administration of Connexin43 Mimetic Peptide Improves Functional Recovery after Traumatic Spinal Cord Injury in Adult Rats." J Neurotrauma 34(3): 707-719.

Marchettini, P., M. Lacerenza, E. Mauri and C. Marangoni (2006). "Painful peripheral neuropathies." Curr Neuropharmacol 4(3): 175-181.

Martinov, T., M. Mack, A. Sykes and D. Chatterjea (2013). "Measuring changes in tactile sensitivity in the hind paw of mice using an electronic von Frey apparatus." J Vis Exp(82): e51212.

Milian, L., "Synthesis and reactive oxygen species scavenging activity of halogenated alkaloids from boldine", Medicinal Chemistry Research (2012), 21(10), 3133-3139.

Nagoshi, N., S. Kaneko, K. Fujiyoshi, M. Takemitsu, M. Yagi, S. lizuka, A. Miyake, A. Hasegawa, M. Machida, T. Konomi, M. Machida, T. Asazuma, and M. Nakamura. 2016. 'Characteristics of neuropathic pain and its relationship with quality of life in 72 patients with spinal cord injury', Spinal Cord, 54: 656-61.

Nuriel, T., S. L. Angulo, U. Khan, A. Ashok, Q. Chen, H. Y. Figueroa, S. Emrani, L. Liu, M. Herman, G. Barrett, V. Savage, L. Buitrago, E. Cepeda-Prado, C. Fung, E. Goldberg, S. S. Gross, S. A. Hussaini, H. Moreno, S. A. Small, and K. E. Duff. 2017. 'Neuronal hyperactivity due to loss of inhibitory tone in APOE4 mice lacking Alzheimer's diseaselike pathology', Nat Commun, 8: 1464.

Nwabuisi-Heath, E., G. W. Rebeck, M. J. Ladu, and C. Yu. 2014. 'ApoE4 delays dendritic spine formation during neuron development and accelerates loss of mature spines in vitro', ASN Neuro, 6: e00134.

O'Brien, P., C. Carrasco-Pozo, and H. Speisky. 2006. 'Boldine and its antioxidant or healthpromoting properties', Chem Biol Interact, 159: 1-17.

O'Carroll, S. J., C. A. Gorrie, S. Velamoor, C. R. Green, and L. F. Nicholson. 2013. 'Connexin43 mimetic peptide is neuroprotective and improves function following spinal cord injury', Neurosci Res, 75: 256-67.

O'Shea, T. M., J. E. Burda, and M. V. Sofroniew. 2017. 'Cell biology of spinal cord injury and repair', J Clin Invest, 127: 3259-70.

Pasala, V.K., "Semi synthesis of open (1,2,9,10) and closed (1,2, & 9, 10) 7-oxoaporphines and related analogues of Boldine" Journal of Applicable Chemistry (2017) 6(5), 817-824.

Parpura, V., E. Scemes, and D. C. Spray. 2004. 'Mechanisms of glutamate release from astrocytes: gap junction "hemichannels", purinergic receptors and exocytotic release', Neurochem Int, 45: 259-64.

Putzke, J. D., J. S. Richards, B. L. Hicken, and M. J. DeVivo. 2002. 'Interference due to pain following spinal cord injury: important predictors and impact on quality of life', Pain, 100: 231-42.

(56) References Cited

OTHER PUBLICATIONS

Retamal, M. A., N. Froger, N. Palacios-Prado, P. Ezan, P. J. Saez, J. C. Saez, and C. Giaume. 2007. 'Cx43 hemichannels and gap junction channels in astrocytes are regulated oppositely by proinflammatory cytokines released from activated microglia', J Neurosci, 27: 13781-92.

Rintala, D. H., P. G. Loubser, J. Castro, K. A. Hart and M. J. Fuhrer (1998). "Chronic pain in a community-based sample of men with spinal cord injury: prevalence, severity, and relationship with impairment, disability, handicap, and subjective well-being." Arch Phys Med Rehabil 79(6): 604-614.

Rouach, N., A. Koulakoff, V. Abudara, K. Willecke, and C. Giaume. 2008. 'Astroglial metabolic networks sustain hippocampal synaptic transmission', Science, 322: 1551-5.

Roy, R. R., and V. R. Edgerton. 2012. 'Neurobiological perspective of spasticity as occurs after a spinal cord injury', Exp Neurol, 235: 116-22.

Schalper, K. A., H. A. Sanchez, S. C. Lee, G. A. Altenberg, M. H. Nathanson, and J. C. Saez. 2010. 'Connexin 43 hemichannels mediate the Ca2+ influx induced by extracellular alkalinization', Am J Physiol Cell Physiol, 299: C1504-15.

Siddall, P. J., J. M. McClelland, S. B. Rutkowski and M. J. Cousins (2003). "A longitudinal study of the prevalence and characteristics of pain in the first 5 years following spinal cord injury." Pain 103(3): 249- 257.

Simard, M., G. Arcuino, T. Takano, Q. S. Liu and M. Nedergaard (2003). "Signaling at the gliovascular interface." J Neurosci 23(27): 9254-9262.

Shintani-Ishida, K., K. Uemura, and K. Yoshida. 2007. 'Hemichannels in cardiomyocytes open transiently during ischemia and contribute to reperfusion injury following brief ischemia', Am J Physiol Heart Circ Physiol, 293: H1714-20.

Sobarzo-Sanchez, E., "New heterocyclic skeletons derived from the aporphine alkaloid boldine" Synthetic Communications (2002), 32(23), 3687-3693.

Theriault, E., U. N. Frankenstein, E. L. Hertzberg, and J. I. Nagy. 1997. 'Connexin43 and astrocytic gap junctions in the rat spinal cord after acute compression injury', J Comp Neurol, 382: 199-214.

Thormet, F. A et al., "Cytotoxic thiocarbamate derivatives of boldine" Natural Product Communications (2010), 5(10) 1587-1590.

Tonkin, R. S., Y. Mao, S. J. O'Carroll, L. F. Nicholson, C. R. Green, C. A. Gorrie, and G. Moalem-Taylor. 2014. 'Gap junction proteins and their role in spinal cord injury', Front Mol Neurosci, 7: 102.

Vavrek, R., J. Girgis, W. Tetzlaff, G. W. Hiebert, and K. Fouad. 2006. 'BDNF promotes connections of corticospinal neurons onto spared descending interneurons in spinal cord injured rats', Brain, 129: 1534-45.

Volterra, A., and J. Meldolesi. 2005. 'Astrocytes, from brain glue to communication elements: the revolution continues', Nat Rev Neurosci, 6: 626-40.

Wallraff, A., R. Kohling, U. Heinemann, M. Theis, K. Willecke and C. Steinhauser (2006). "The impact of astrocytic gap junctional coupling on potassium buffering in the hippocampus." J Neurosci 26(20): 5438- 5447.

Widerstrom-Noga, E., F. Biering-Sorensen, T. Bryce, D. D. Cardenas, N. B. Finnerup, M. P. Jensen, J. S. Richards, and P. J. Siddall. 2008. 'The international spinal cord injury pain basic data set', Spinal Cord, 46: 818-23.

Wu, J., C. Raver, C. Piao, A. Keller and A. I. Faden (2013). "Cell cycle activation contributes to increased neuronal activity in the posterior thalamic nucleus and associated chronic hyperesthesia after rat spinal cord contusion." Neurotherapeutics 10(3): 520-538.

Wu, J., C. L. Renn, A. I. Faden and S. G. Dorsey (2013). "TrkB.T1 contributes to neuropathic pain after spinal cord injury through regulation of cell cycle pathways." J Neurosci 33(30): 12447-12463.

Wu, J., B. A. Stoica, T. Luo, B. Sabirzhanov, Z. Zhao, K. Guanciale, S. K. Nayar, C. A. Foss, M. G. Pomper and A. I. Faden (2014). "Isolated spinal cord contusion in rats induces chronic brain neuroinflammation, neurodegeneration, and cognitive impairment. Involvement of cell cycle activation." Cell Cycle 13(15): 2446-2458.

Xie, H. Y., Y. Cui, F. Deng, and J. C. Feng. 2015. 'Connexin: a potential novel target for protecting the central nervous system?', Neural Regen Res, 10: 659-66.

Yates, C., A. Charlesworth, S. R. Allen, N. B. Reese, R. D. Skinner, and E. Garcia-Rill. 2008. 'The onset of hyperreflexia in the rat following complete spinal cord transection', Spinal Cord, 46: 798-803.

M, C., P. Ezan, P. Fernandez, J. Schmitt, J. C. Saez, C. Giaume, and A. Koulakoff. 2017. 'Inhibition of glial hemichannels by boldine treatment reduces neuronal suffering in a murine model of Alzheimer's disease', Glia, 65: 1607-25.

Zhao, W., L. Ho, M. Varghese, S. Yemul, K. Dams-O'Connor, W. Gordon, L. Knable, D. Freire, V. Haroutunian and G. M. Pasinetti (2013). "Decreased level of olfactory receptors in blood cells following traumatic brain injury and potential association with tauopathy." J Alzheimers Dis 34(2): 417-429.

Zhao, W., L. Ho, J. Wang, W. Bi, S. Yemul, L. Ward, D. Freire, P. Mazzola, J. Brathwaite, M. Mezei, R. Sanchez, G. A. Elder and G. M. Pasinetti (2016). "In Silico Modeling of Novel Drug Ligands for Treatment of Concussion Associated Tauopathy." J Cell Biochem 117(10): 2241-2248.

Ahuja, C.S., et al., The leading edge: Emerging neuroprotective and neuroregenerative cell-based therapies for spinal cord injury. Stem Cells Transl Med, 2020. 9(12): p. 1509-1530.

Badhiwala, J.H., C.S. Ahuja, and M.G. Fehlings, *Time is spine: a review of translational advances in spinal cord injury*. J Neurosurg Spine, 2018. 30(1): p. 1-18.

Wang, X., et al., P2X7 receptor inhibition improves recovery after spinal cord injury. Nat Med, 2004. 10(8): p. 821-7.

Spray, D.C. and M. Hanani, Gap junctions, pannexins and pain. Neurosci Lett, 2019. 695: p. 46-52.

Abou-Mrad, Z., et al., Role of connexins in spinal cord injury: An update. Clin Neurol Neurosurg, 2020. 197: p. 106102.

Munoz, M.F., T.N. Griffith, and J.E. Contreras, Mechanisms of ATP release in pain: role of pannexin and connexin channels. Purinergic Signal, 2021. 17(4): p. 549-561.

Cisterna, B.A., C. Cardozo, and J.C. Saez, *Neuronal involvement in muscular atrophy*. Front Cell Neurosci, 2014. 8: p. 405.

Sáez, J.C., et al., Regulation of pannexin and connexin channels and their functional role in skeletal muscles. Cell Mol Life Sci, 2015. 72(15): p. 2929-35.

Giaume, C., et al., Glial Connexins and Pannexins in the Healthy and Diseased Brain. Physiol Rev, 2021. 101(1): p. 93-145.

Yi, C., et al., Inhibition of glial hemichannels by boldine treatment reduces neuronal suffering in a murine model of Alzheimer's disease. Glia, 2017. 65(10): p. 1607-1625.

Garcia-Rodriguez, C., et al., Contribution of non-selective membrane channels and receptors in epilepsy. Pharmacol Ther, 2022. 231: p. 107980.

Di Virgilio, F., et al., The P2Z/P2X7 receptor of microglial cells: a novel immunomodulatory receptor. Prog Brain Res, 1999. 120: p. 355-68.

Peng, W., et al., Systemic administration of an antagonist of the ATP-sensitive receptor P2X7 improves recovery after spinal cord injury. Proc Natl Acad Sci U S A, 2009. 106(30): p. 12489-93.

Toro, C.A., et al., The Human ApoE4 Variant Reduces Functional Recovery and Neuronal Sprouting After Incomplete Spinal Cord Injury in Male Mice. Front Cell Neurosci, 2021. 15: p. 626192.

Scheff, S.W., et al., Experimental modeling of spinal cord injury: characterization of a force-defined injury device. J Neurotrauma, 2003. 20(2): p. 179-93.

Cummings, B.J., et al., Adaptation of a ladder beam walking task to assess locomotor recovery in mice following spinal cord injury. Behav Brain Res, 2007. 177(2): p. 232-41.

Wang, F., et al., RNAscope: a novel in situ RNA analysis platform for formalin-fixed, paraffin-embedded tissues. J Mol Diagn, 2012. 14(1): p. 22-9.

Oliveira, A.L., et al., A role for MHC class I molecules in synaptic plasticity and regeneration of neurons after axotomy. Proc Natl Acad Sci U S A, 2004. 101(51): p. 17843-8.

(56) References Cited

OTHER PUBLICATIONS

Toro, C.A., et al., Trithorax dependent changes in chromatin landscape at enhancer and promoter regions drive female puberty. Nat Commun, 2018. 9(1): p. 57.
Mariottini, C., et al., *Wilm's tumor 1 promotes memory flexibility.* Nat Commun, 2019. 10(1): p. 3756.
Stillitano, F., et al., Modeling susceptibility to drug-induced long QT with a panel of subject-specific induced pluripotent stem cells. Elife, 2017. 6.
Hansen, J., et al., Systems pharmacology-based integration of human and mouse data for drug repurposing to treat thoracic aneurysms. JCI Insight, 2019. 4(11).
Chen, E.Y., et al., Enrichr: interactive and collaborative HTML5 gene list enrichment analysis tool. BMC Bioinformatics, 2013. 14: p. 128.
Shah, P.K., et al., Use of quadrupedal step training to re-engage spinal interneuronal networks and improve locomotor function after spinal cord injury. Brain, 2013. 136(Pt 11): p. 3362-77.
Kerstetter, A.E. and R.H. Miller, *Isolation and Culture of Spinal Cord Astrocytes, in Astrocytes: Methods and Protocols*, R. Milner, Editor. 2012, Humana Press: Totowa, NJ. p. 93-104.
Koshimizu, T., M. Koshimizu, and S.S. Stojilkovic, *Contributions of the C-terminal domain to the control of P2X receptor desensitization.* J Biol Chem, 1999. 274(53): p. 37651-7.
Brenner, M., *Role of GFAP in CNS injuries.* Neurosci Lett, 2014. 565: p. 7-13.
Peng, S., et al., Precursor form of brain-derived neurotrophic factor and mature brain-derived neurotrophic factor are decreased in the pre-clinical stages of Alzheimer's disease. J Neurochem, 2005. 93(6): p. 1412-21.
Miller, A.D., et al., Acute traumatic spinal cord injury induces glial activation in the cynomolgus macaque (*Macaca fascicularis*). J Med Primatol, 2012. 41(3): p. 202-9.
Koshi, T., et al., Lumbar posterolateral fusion inhibits sensory nerve ingrowth into punctured lumbar intervertebral discs and upregulation of CGRP immunoreactive DRG neuron innervating punctured discs in rats. Eur Spine J, 2010. 19(4): p. 593-600.
Rash, J.E., et al., Identification of cells expressing Cx43, Cx30, Cx26, Cx32 and Cx36 in gap junctions of rat brain and spinal cord. Cell Commun Adhes, 2001. 8(4-6): p. 315-20.
Nagy, J.I., et al., Coupling of astrocyte connexins Cx26, Cx30, Cx43 to oligodendrocyte Cx29, Cx32, Cx47: Implications from normal and connexin32 knockout mice. Glia, 2003. 44(3): p. 205-18.
Anselmi, F., et al., ATP release through connexin hemichannels and gap junction transfer of second messengers propagate Ca2+ signals across the inner ear. Proc Natl Acad Sci U S A, 2008. 105(48): p. 18770-5.
Yu, C.W., et al., Pro-inflammatory cytokines IL-6 and CCL2 suppress expression of circadian gene Period2 in mammary epithelial cells. Biochim Biophys Acta Gene Regul Mech, 2018. 1861(11): p. 1007-1017.
Mooren, F.C., et al., The response of the novel pro-inflammatory molecules S100A8/A9 to exercise. Int J Sports Med, 2006. 27(9): p. 751-8.
Brown, C.M., et al., Production of proinflammatory cytokines and chemokines during neuroinflammation: novel roles for estrogen receptors alpha and beta. Endocrinology, 2010. 151(10): p. 4916-25.
Xuan, F.L., et al., *Differences of Microglia in the Brain and the Spinal Cord.* Front Cell Neurosci, 2019. 13: p. 504.
Spiller, K.J., et al., Reduction of matrix metalloproteinase 9 (MMP-9) protects motor neurons from TDP-43-triggered death in rNLS8 mice. Neurobiol Dis, 2019. 124: p. 133-140.
Antonucci, F., et al., SNAP-25, a Known Presynaptic Protein with Emerging Postsynaptic Functions. Front Synaptic Neurosci, 2016. 8: p. 7.
Zhong, J., et al., Expression of mRNAs encoding subunits of the NMDA receptor in developing rat brain. J Neurochem, 1995. 64(2): p. 531-9.
Ryden, M., B. Hempstead, and C.F. Ibanez, Differential modulation of neuron survival during development by nerve growth factor binding to the p75 neurotrophin receptor. J Biol Chem, 1997. 272(26): p. 16322-8.
Hayakawa, K., et al., Phosphorylated neurofilament subunit NF-H as a biomarker for evaluating the severity of spinal cord injury patients, a pilot study. Spinal Cord, 2012. 50(7): p. 493-6.
Turney, S.G., et al., Nerve growth factor stimulates axon outgrowth through negative regulation of growth cone actomyosin restraint of microtubule advance. Mol Biol Cell, 2016. 27(3): p. 500-17.
Fornaro, M., et al., Role of neurotrophic factors in enhancing linear axonal growth of ganglionic sensory neurons in vitro. Neural Regen Res, 2020. 15(9): p. 1732-1739.
Sluyter, R. and L. Stokes, *Significance of P2X7 receptor variants to human health and disease.* Recent Pat DNA Gene Seq, 2011. 5(1): p. 41-54.
Zhang, C., et al., Inhibition of astrocyte hemichannel improves recovery from spinal cord injury. JCI Insight, 2021. 6(5).
Basso, D.M., M.S. Beattie, and J.C. Bresnahan, Graded histological and locomotor outcomes after spinal cord contusion using the NYU weight-drop device versus transection. Exp Neurol, 1996. 139(2): p. 244-56.
Alizadeh, A., S.M. Dyck, and S. Karimi-Abdolrezaee, Traumatic Spinal Cord Injury: An Overview of Pathophysiology, Models and Acute Injury Mechanisms. Front Neurol, 2019. 10: p. 282.
Bareyre, F.M., et al., The injured spinal cord spontaneously forms a new intraspinal circuit in adult rats. Nat Neurosci, 2004. 7(3): p. 269-77.
Asboth, L., et al., Cortico-reticulo-spinal circuit reorganization enables functional recovery after severe spinal cord contusion. Nat Neurosci, 2018. 21(4): p. 576-588.
Russ, D.E., et al., A harmonized atlas of mouse spinal cord cell types and their spatial organization. Nat Commun, 2021. 12(1): p. 5722.
U.S. Appl. No. 62/971,757, filed Feb. 7, 2020, Christopher Cardozo.
U.S. Appl. No. 63/043,572, filed Jun. 24, 2020, Christopher Cardozo.
U.S. Appl. No. 17/170,821, filed Feb. 8, 2021, Christopher Cardozo.
U.S. Appl. No. 63/483,533, filed Feb. 6, 2023, Christopher Cardozo.

\* cited by examiner

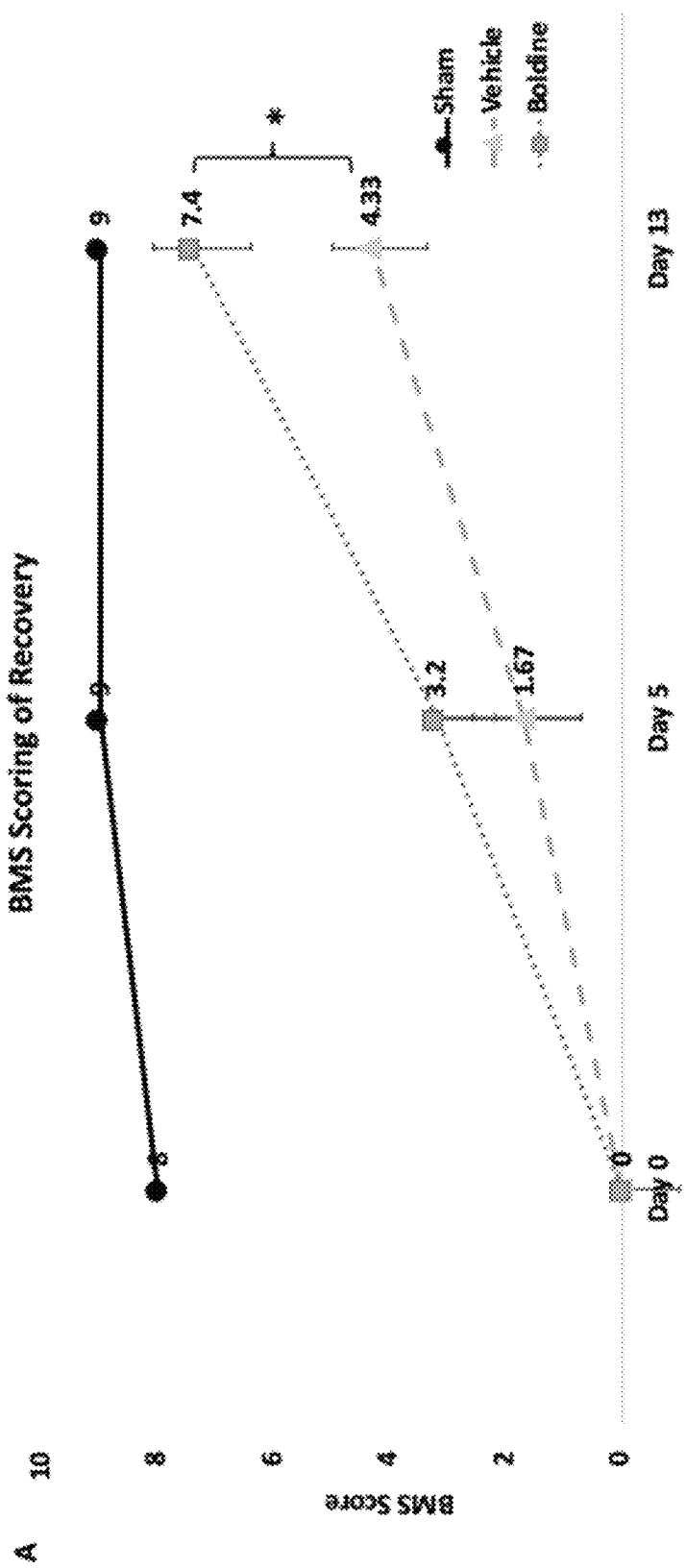

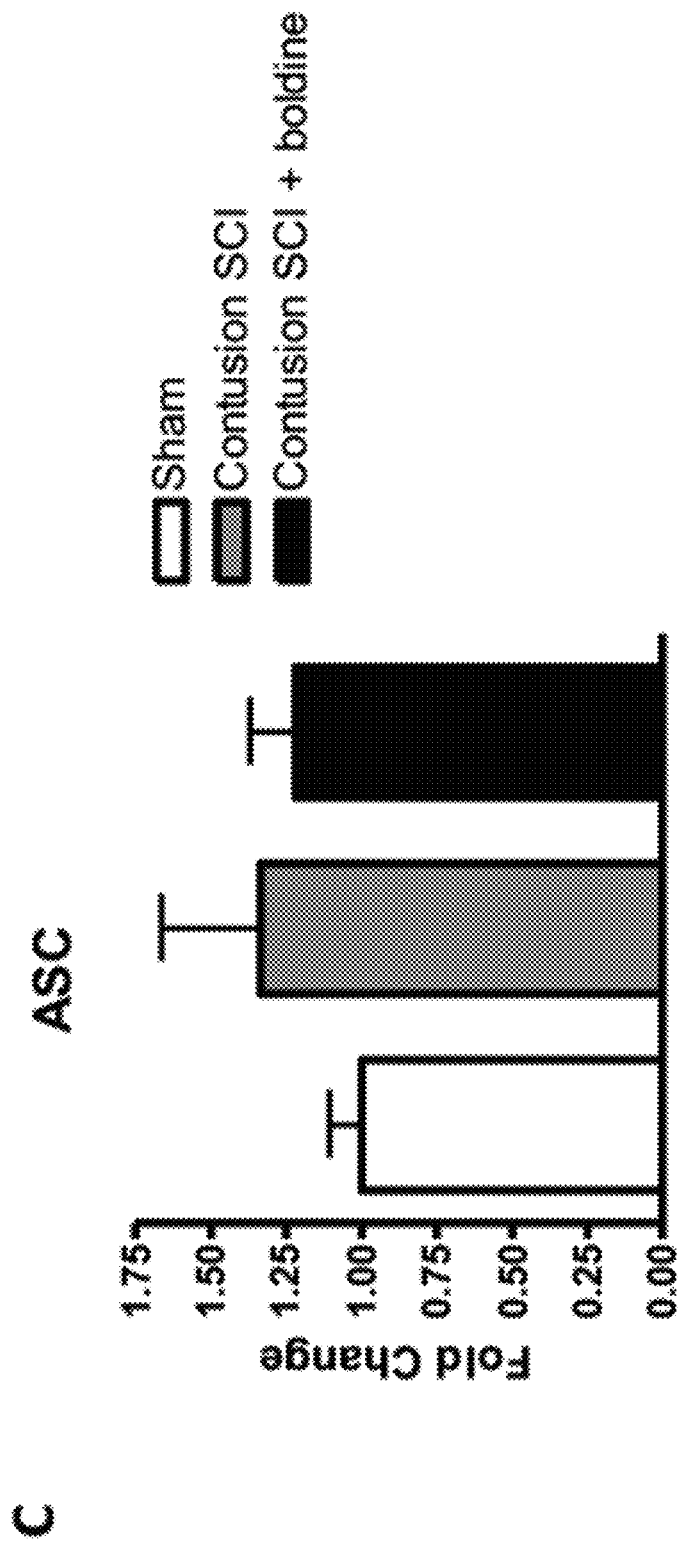

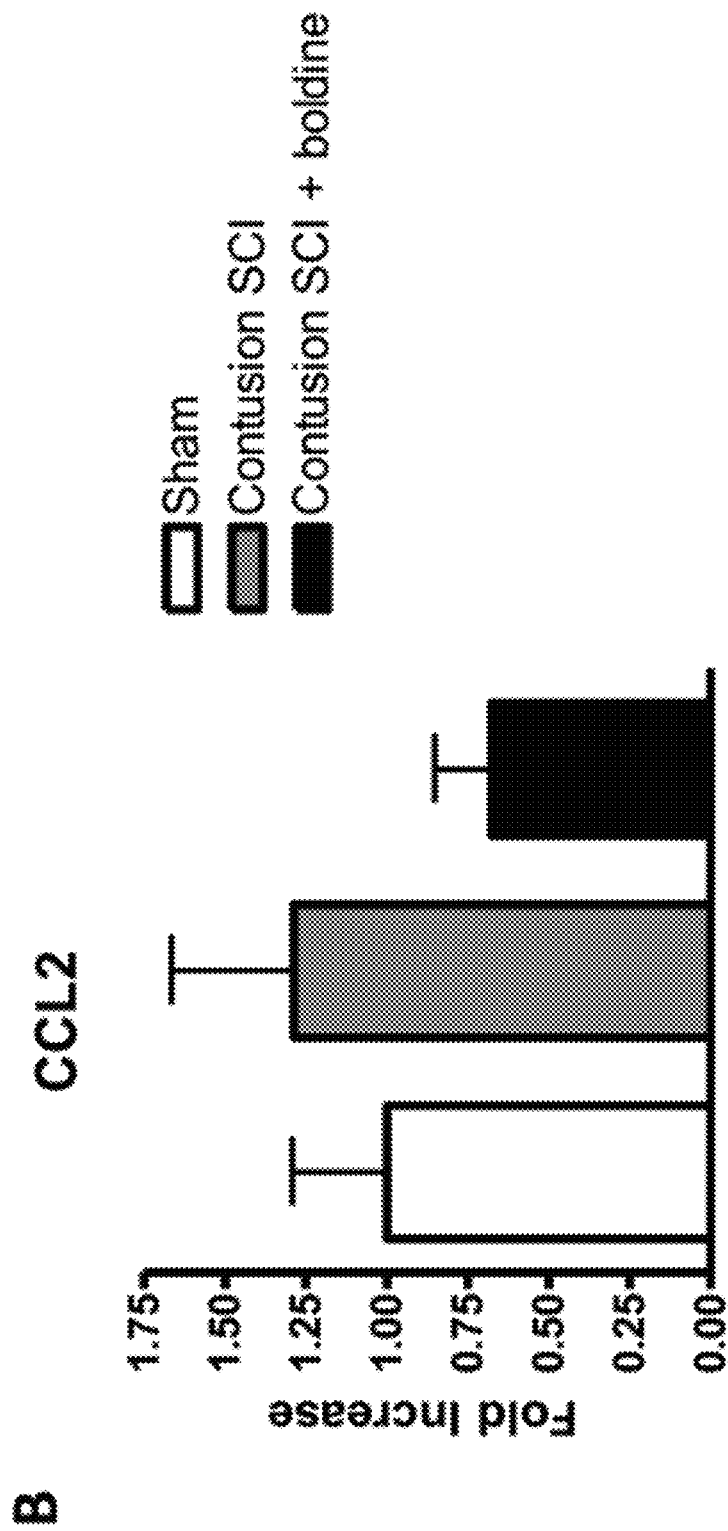

METHOD FOR TREATING NERVOUS SYSTEM INJURIES USING BOLDINE AND DERIVATIVES THEREOF

CROSS-REFERENCE TO RELATED APPLICATIONS

This application is a divisional of U.S. application Ser. No. 17/170,821, filed Feb. 8, 2021, which claims the benefit of U.S. Provisional Application No. 62/971,757, filed Feb. 7, 2020, and U.S. Provisional Application No. 63/043,572, filed Jun. 24, 2020, the contents of which are incorporated herein by reference in their entireties.

BACKGROUND

The mammalian nervous system comprises a peripheral nervous system (PNS) and a central nervous system (CNS, comprising the brain and spinal cord), and is composed of two principal classes of cells: neurons and glial cells. The glial cells fill the spaces between neurons, nourishing them and modulating their function. Certain glial cells, such as Schwann cells in the PNS and oligodendrocytes in the CNS, also provide a protective myelin sheath that surrounds and protects neuronal axons, which are the processes that extend from the neuron cell body and through which the electric impulses of the neuron are transported. In the peripheral nervous system, the long axons of multiple neurons are bundled together to form a nerve or nerve fiber. These, in turn, may be combined into fascicles, wherein the nerve fibers form bundles embedded, together with the intraneural vascular supply, in a loose collagenous matrix bounded by a protective multilamellar sheath. In the central nervous system, the neuron cell bodies are visually distinguishable from their myelin-ensheathed processes, and are referenced in the art as gray and white matter, respectively.

The nervous system stimulates many tissues in the body and by doing so affects the perception of pain, joint position, muscle tension, hot and cold sensations, pulse, blood pressure, salivation, eye function, intestine function, among other physiological processes. Similarly, nerves transmit impulses by which the brain signals which muscles to contract. Accordingly, the neural pathways of a mammal are particularly at risk if neurons are subjected to trauma.

Injuries to the nervous system frequently disrupt nerve function and interfere with various physiological processes regulated or controlled by nerves. Injuries to the central nervous system, for example, such as a spinal cord injury (SCI), can be devastating, often resulting in paralysis, loss of sensation, dysregulation of the automatic nervous system, and inability to regain voluntary control of muscles. Likewise, traumatic brain injury (TBI), often caused by blunt trauma, often results in immediate neuronal, axonal, and vascular destruction. Peripheral nerve injuries, such as a crushed nerve as a result of trauma, can also result in disruption to nervous system function. Finally, nervous system injuries often lead to secondary conditions such as neuropathic pain, which is difficult to ameliorate with conventional pain medications, in addition to loss or impairment of voluntary muscle control and locomotor function.

Though strides have been made toward addressing complications of nervous system injuries, such as pulmonary or bladder complications, there is no cell-based or pharmacologic approach to consistently improve sensory or motor function after a traumatic injury to the nervous system. Thus, there remains a need for effective treatment of various injuries to the nervous system, as well as secondary conditions that may arise from such injuries, including neuropathic pain. These needs and others are met by the following disclosure.

SUMMARY

In one aspect, this disclosure relates to a method of treating an injury to the nervous system in a subject, comprising administering to the subject an effective amount of a compound represented by the formula:

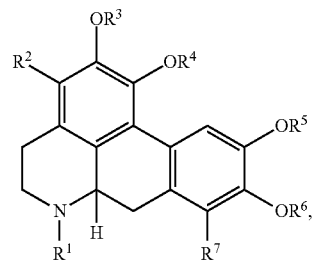

wherein $R^1$ is selected from hydrogen and C1-C4 alkyl; wherein $R^2$ is selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^3$ and $R^4$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^3$ and $R^4$ join together to form a ring having 5-7 atoms; wherein each of $R^5$ and $R^6$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^5$ and $R^6$ join together to form a ring having 5-7 atoms; and wherein $R^7$ is selected from hydrogen, halogen, —CN, —$NH_2$, —OH, —$NO_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or a pharmaceutically-acceptable salt thereof, thereby treating the injury to the nervous system in the subject.

In a further aspect, the disclosure relates to a method of improving voluntary muscle control in a subject having an injury to the nervous system, comprising administering to the subject an effective amount of a compound represented by the formula:

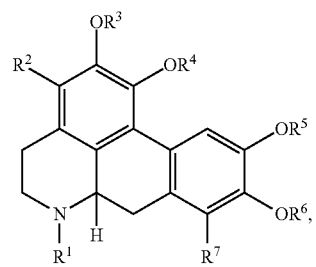

wherein $R^1$ is selected from hydrogen and C1-C4 alkyl; wherein $R^2$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^3$ and $R^4$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^3$ and $R^4$ join together to form a ring having 5-7 atoms; wherein each of $R^5$ and $R^6$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^5$ and $R^6$ join together to form a ring having 5-7 atoms; and wherein $R^7$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or a pharmaceutically-acceptable salt thereof, thereby improving voluntary muscle control in the subject.

In a further aspect, disclosed is a method of treating neuropathic pain in a subject having an injury to the nervous system, comprising administering to the subject an effective amount of a compound represented by the formula:

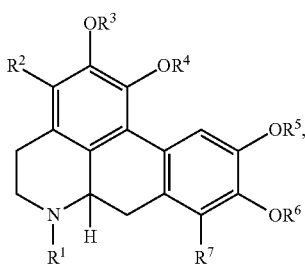

wherein $R^1$ is selected from hydrogen and C1-C4 alkyl; wherein $R^2$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^3$ and $R^4$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^3$ and $R^4$ join together to form a ring having 5-7 atoms; wherein each of $R^5$ and $R^6$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^5$ and $R^6$ join together to form a ring having 5-7 atoms; and wherein $R^7$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or a pharmaceutically-acceptable salt thereof, thereby treating neuropathic pain in the subject.

Still other objects and advantages of the present disclosure will become readily apparent by those skilled in the art from the following detailed description, which is shown and described by reference to preferred aspects, simply by way of illustration of the best mode. As will be realized, the disclosure is capable of other and different aspects, and its several details are capable of modifications in various respects, without departing from the disclosure. Accordingly, the description is to be regarded as illustrative in nature and not as restrictive.

BRIEF DESCRIPTION OF THE DRAWINGS

The accompanying drawings, which are incorporated in and constitute a part of this specification and together with the description, serve to explain the principles of the disclosure.

FIGS. 1A-C show the effects of boldine on locomotor functional recovery of C57BL6 mice after moderate spinal cord injury (SCI) at the interspace between thoracic vertebrae T9 and T10. FIG. 1A shows Basso Mouse Scale (BMS) scores to examine open-field locomotor function after 5- and 13-days post injury on sham, and vehicle or boldine treated animals. FIG. 1B shows a plot derived from the ladder rung walk test (LRWT), which describes the recovery of fine motor skills of mice, particularly the number of missed foot placements, in percentage, when comparing vehicle to boldine treated SCI animals at 13 dpi. FIG. 1C shows a timeline of the studies performed.

FIGS. 2A-D show plots of mRNA levels of Cx43 (2A), NLRP3 (2B), ASC (2C), and caspase-1 (2D) in the hippocampus of sham mice and those having contusion spinal cord injury (SCI) with and without boldine treatment. mRNA levels in the hippocampus were determined by qPCR at 13 dpi using tissues from mice that underwent laminectomy (Sham) or moderate (50 kdyne) contusion SCI. ((*$p<0.05$ by one-way ANOVA, N=3 per group).

FIGS. 3A-B are plots showing that boldine normalizes spinal cord injury (SCI)-induced elevation of IL-1B mRNA levels in the thalamus. mRNA levels were determined as described with reference to FIG. 2. (A) IL-1β; (B) CCL2. (*$p<0.05$ by ANOVA, N=3).

DETAILED DESCRIPTION

Figure 1B:
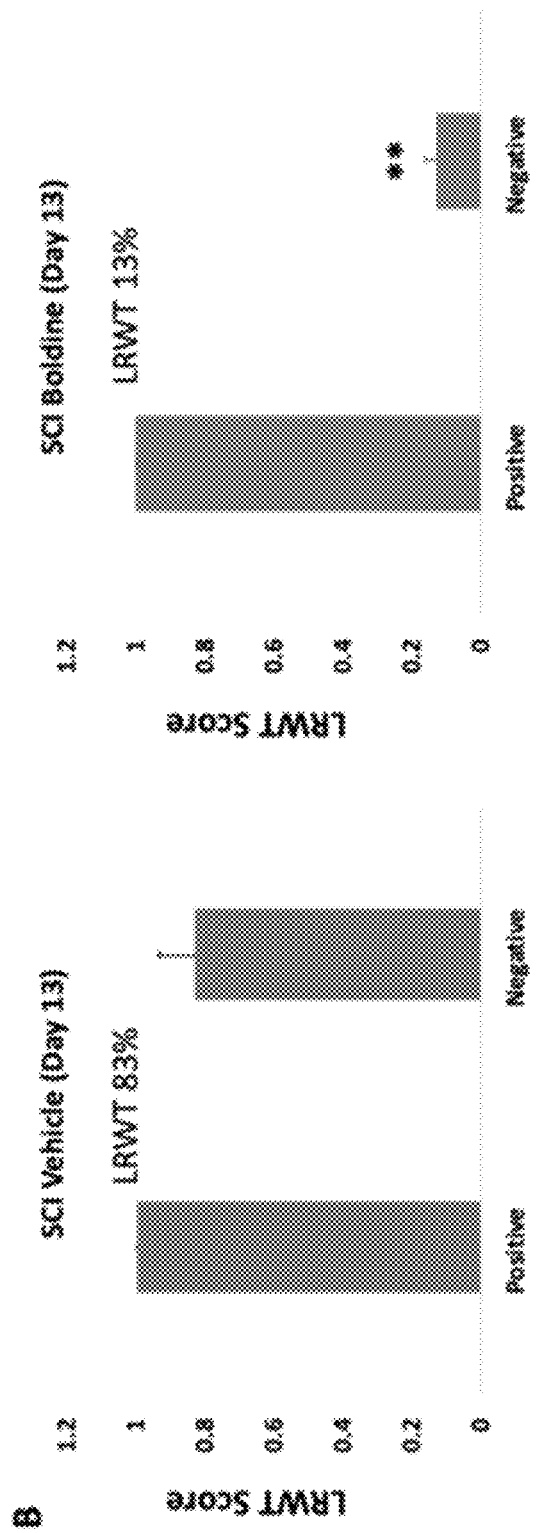

The present invention can be understood more readily by reference to the following detailed description of the invention and the Examples included therein.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present compositions, methods, and kits may be understood more readily by reference to the following detailed description of preferred embodiments and the examples included therein.

While aspects of this disclosure can be described and claimed in a particular statutory class, such as the system statutory class, this is for convenience only and one of skill in the art will understand that each aspect of this disclosure can be described and claimed in any statutory class. Unless otherwise expressly stated, it is in no way intended that any method or aspect set forth herein be construed as requiring that its steps be performed in a specific order. Accordingly, where a method claim does not specifically state in the claims or description that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Nothing herein is to be construed as an admission that the present application is not entitled to antedate such publication by virtue of prior invention. Further, stated publication dates may be different from actual publication dates, which can require independent confirmation.

A. Definitions

Listed below are definitions of various terms used to describe this invention. These definitions apply to the terms as they are used throughout this specification, unless otherwise limited in specific instances, either individually or as part of a larger group.

As used in the specification and in the claims, the term "comprising" can include the aspects "consisting of" and "consisting essentially of."

As used in the specification and claims, the singular forms "a," "an," and "the" include plural referents unless the context clearly dictates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "about" and "at or about" mean that the amount or value in question can be the value designated some other value approximately or about the same. It is generally understood, as used herein, that it is the nominal value indicated ±10% variation unless otherwise indicated or inferred. The term is intended to convey that similar values promote equivalent results or effects recited in the claims. That is, it is understood that amounts, sizes, formulations, parameters, and other quantities and characteristics are not and need not be exact, but can be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. It is understood that where "about" is used before a quantitative value, the parameter also includes the specific quantitative value itself, unless specifically stated otherwise.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, "$IC_{50}$" is intended to refer to the concentration of a substance (e.g., a compound or a drug) that is required for 50% inhibition of a biological process, or component of a process, including a protein, subunit, organelle, ribonucleoprotein, etc. In one aspect, an $IC_{50}$ can refer to the concentration of a substance that is required for 50% inhibition in vivo, as further defined elsewhere herein. In a further aspect, $IC_{50}$ refers to the half-maximal (50%) inhibitory concentration (IC) of a substance.

As used herein, "$EC_{50}$" is intended to refer to the concentration of a substance (e.g., a compound or a drug) that is required for 50% agonism of a biological process, or component of a process, including a protein, subunit, organelle, ribonucleoprotein, etc. In one aspect, an $EC_{50}$ can refer to the concentration of a substance that is required for 50% agonism in vivo, as further defined elsewhere herein. In a further aspect, $EC_{50}$ refers to the concentration of agonist that provokes a response halfway between the baseline and maximum response.

"Optional" or "optionally" means that the subsequently described event or circumstance may or may not occur, and that the description includes instances where said event or circumstance occurs and instances where it does not.

The term "analog" as used herein refers to a chemical compound that is structurally related to boldine. The analog can be prepared from boldine or other suitable starting materials, and thus the term "analog" does not necessarily imply that the compound was derived from or prepared from boldine.

The term "pharmaceutically acceptable salt," as used herein, refers to an inorganic or organic salt of a disclosed compound that is suitable for administration to a subject.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "by weight," when used in conjunction with a component, unless specially stated to the contrary is based on the total weight of the formulation or composition in which the component is included. For example, if a particular element or component in a composition or article is said to have 8% by weight, it is understood that this percentage is in relation to a total compositional percentage of 100%.

A weight percent of a component, or weight %, or wt %, unless specifically stated to the contrary, is based on the total weight of the formulation or composition in which the component is included.

As used herein, the term "subject" can be a vertebrate, such as a mammal, a fish, a bird, a reptile, or an amphibian. Thus, the subject can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with an ailment, disease, or disorder. The term "patient" includes human and veterinary subjects.

As used herein, the terms "treatment" and "treating" refer to the medical management of a subject with the intent to cure, ameliorate, stabilize, or prevent an ailment, disease, pathological condition, disorder, or injury. This term includes active treatment, that is, treatment directed specifically toward the improvement of a disease, pathological condition, disorder, or injury, and also includes causal treatment, that is, treatment directed toward removal of the cause of the associated disease, pathological condition, disorder, or injury. In addition, this term includes palliative treatment, that is, treatment designed for the relief of symptoms rather than the curing of the disease, pathological condition, disorder, or injury; preventative treatment, that is, treatment directed to minimizing or partially or completely inhibiting the development of the associated disease, pathological condition, disorder, or injury; and supportive treatment, that is, treatment employed to supplement another specific therapy directed toward the improvement of the associated disease, pathological condition, disorder, or injury. In various aspects, the term covers any treatment of a subject, including a mammal (e.g., a human), and includes: (i) preventing the disorder or condition from occurring in a subject that can be predisposed to the disorder or condition but has not yet been diagnosed as having it; (ii) inhibiting the disorder or condition, i.e., arresting its development or exacerbation thereof; or (iii) relieving the disorder or condition, i.e., promoting healing of the disorder or condition. In one aspect, the subject is a mammal such as a primate, and, in a further aspect, the subject is a human.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by a disclosed compound.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

The "central nervous system" (CNS) includes the brain, spinal cord, optic, olfactory, and auditory systems. The CNS comprises both neurons and glial cells (neuroglia), which are support cells that aid the function of neurons. Oligodendrocytes, astrocytes, and microglia are glial cells within the CNS. Oligodendrocytes myelinate axons in the CNS, while astrocytes contribute to the blood-brain barrier, which separates the CNS from blood proteins and cells, and perform a number of supportive functions for neurons. Microglial cells serve immune system functions.

The "peripheral nervous system" (PNS), for purposes of this disclosure, includes the cranial nerves arising from the brain (other than the optic and olfactory nerves), the spinal nerves arising from the spinal cord, sensory nerve cell bodies, and their processes, i.e., all nervous tissue outside of the CNS. The PNS comprises both neurons and glial cells (neuroglia), which are support cells that aid the function of neurons. Glial cells within the PNS are known as Schwann cells, and serve to myelinate axons by providing a sheath that surrounds the axons. In various aspects, the methods and compositions described herein can be applied to different portions of the PNS.

The term "injury to the nervous system," including the central or peripheral nervous system, refers to any injury to the nervous system caused by trauma instead of disease (e.g., a disease such as cancer).

The term "central nervous system injury" refers to any injury to the central nervous system caused by trauma instead of disease (e.g., a disease such as cancer). The term encompasses injuries to the central nervous system that result in loss or impairment of motor function, sensory function, or a combination thereof.

As used herein, "traumatic brain injury" or "TBI" refers to an acquired brain injury or head injury in which trauma damages the brain. The damage can be localized, i.e., limited to one area of the brain, or diffuse, affecting one or more areas of the brain.

The term "spinal cord injury," as used herein, means any injury to the spinal cord that is caused by trauma instead of disease (e.g., a disease such as cancer). Depending on where the spinal cord and nerve roots are damaged, the symptoms can vary widely, for example from pain to paralysis to incontinence. Spinal cord injuries are described at various levels of "incomplete," which can vary from having no effect on the subject to a "complete" injury which means a total loss of function. Spinal cord injuries have many causes, but are typically associated with major trauma from motor vehicle accidents, falls, sports injuries, and violence. The abbreviation "SCI" means spinal cord injury.

"Spinal cord contusion," as used herein, refers to an injury caused by trauma instead of disease in which part of the spinal cord is crushed with part of its tissue spared, particularly the ventral nerve fibers connecting the spinal cord rostral and caudal to the injury.

The term "peripheral nervous system injury," as used herein, refers to any injury to a peripheral nerve caused by trauma instead of disease (e.g., a disease such as cancer). "Peripheral nerve injury" encompasses all degrees of nerve injury, including the lowest degree of nerve injury in which the nerve remains intact but signaling ability is damaged, known as neurapraxia. The term also includes the second degree in which the axon is damaged but the surrounding connecting tissue remains intact, known as axonotmesis. Finally, the term encompasses the last degree in which both the axon and connective tissue are damaged, known as neurotmesis.

The term "nerve crush injury," as used herein, refers to traumatic compression of the nerve from a blunt object, such as a bat, surgical clamp or other crushing object that does not result in a complete transection of the nerve.

The term "neuropathic pain," as used herein, refers to chronic pain resulting from injury to the nervous system caused by trauma instead of disease (e.g., a disease such as cancer or diabetes). The injury resulting in neuropathic pain can be to the central nervous system (brain and spinal cord) or the peripheral nervous system (nerves outside the brain and spinal cord).

As used herein, "dosage form" means a pharmacologically active material in a medium, carrier, vehicle, or device suitable for administration to a subject. A dosage forms can comprise inventive a disclosed compound, a product of a disclosed method of making, or a salt, solvate, or polymorph thereof, in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed compound, a product of a disclosed method of making, or a salt, solvate, or polymorph thereof, suspended in sterile saline solution for injection together with a preservative.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as a recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; anti-cancer and antineoplastic agents such as kinase inhibitors, poly ADP ribose polymerase (PARP) inhibitors and other DNA damage response modifiers, epigenetic agents such as bromodomain and extra-terminal (BET) inhibitors, histone deacetylase (HDAc) inhibitors, iron chelotors and other ribonucleotides reductase inhibitors, proteasome inhibitors and Nedd8-activating enzyme (NAE) inhibitors, mammalian target of rapamycin (mTOR) inhibitors, traditional cytotoxic agents such as paclitaxel, dox, irinotecan, and platinum compounds, immune checkpoint blockade agents such as cytotoxic T lymphocyte antigen-4 (CTLA-4) monoclonal antibody (mAB), programmed cell death protein 1 (PD-1)/programmed cell death-ligand 1 (PD-L1) mAB, cluster of differentiation 47 (CD47) mAB, toll-like receptor (TLR) agonists and other immune modifiers, cell therapeutics such as chimeric antigen receptor T-cell (CAR-T)/chimeric antigen receptor natural killer (CAR-NK) cells, and proteins such as interferons (IFNs), interleukins (ILs), and mAbs; anti-ALS agents such as entry inhibitors, fusion inhibitors, non-nucleoside reverse transcriptase inhibitors (NNRTIs), nucleoside reverse transcriptase inhibitors (NRTIs), nucleotide reverse transcriptase inhibitors, NCP7 inhibitors, protease inhibitors, and integrase inhibitors; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term "therapeutic agent" also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, the term "substantially," in, for example, the context "substantially free of" refers to a composition having less than about 10% by weight, e.g., less than about 5%, less than about 1%, less than about 0.5%, less than about 0.1%, less than about 0.05%, or less than about 0.01% by weight of the stated material, based on the total weight of the composition.

It is further understood that the term "substantially," when used in reference to a composition, refers to at least about 60% by weight, e.g., at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or about 100% by weight, based on the total weight of the composition, of a specified feature, component, or a combination of the components. It is further understood that if the composition comprises more than one component, the two or more components can be present in any ratio predetermined by one of ordinary skill in the art.

As used herein, the term "derivative" refers to a compound having a structure similar to the structure of a certain compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, and amides, salts of esters or amides, and N-oxides of a parent compound.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

The term "aliphatic" or "aliphatic group," as used herein, denotes a hydrocarbon moiety that may be straight chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a non-aromatic carbon-based ring type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula $-(CH_2)_a-$, where "a" is an integer of from 2 to 500.

The terms "alkoxy" and "alkoxyl" as used herein to refer to an alkyl or cycloalkyl group bonded through an ether linkage; that is, an "alkoxy" group can be defined as $-OA^1$ where $A^1$ is alkyl or cycloalkyl as defined above. "Alkoxy" also includes polymers of alkoxy groups as just described; that is, an alkoxy can be a polyether such as $-OA^1-OA^2$ or $-OA^1-(OA^2)_a-OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —NH$_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl can be two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —NA$^1$A$^2$, where A$^1$ and A$^2$ can be, independently, hydrogen or alkyl, cycloalkyl, alkenyl, cycloalkenyl, alkynyl, cycloalkynyl, aryl, or heteroaryl group as described herein. A specific example of amino is —NH$_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl)amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The terms "halo," "halogen," or "halide," as used herein can be used interchangeably and refer to F, Cl, Br, or I.

The terms "pseudohalide," "pseudohalogen," or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group that has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxyl" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azide" or "azido" as used herein is represented by the formula —$N_3$.

The term "nitro" as used herein is represented by the formula —$NO_2$.

The term "nitrile" or "cyano" as used herein is represented by the formula —CN.

The term "silyl" as used herein is represented by the formula —$SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —$S(O)A^1$, $S(O)_2A^1$, —$OS(O)_2A^1$, or —$OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula —$S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogen of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; —$(CH_2)_{0-4}R^\circ$; —$(CH_2)_{0-4}OR^\circ$; —$O(CH_2)_{0-4}R^\circ$, —O—$(CH_2)_{0-4}C(O)OR^\circ$; —$(CH_2)_{0-4}CH(OR^\circ)_2$; —$(CH_2)_{0-4}SR^\circ$; —$(CH_2)_{0-4}Ph$, which may be substituted with $R^\circ$; —$(CH_2)_{0-4}O(CH_2)_{0-1}Ph$ which may be substituted with $R^\circ$; —CH=CHPh, which may be substituted with $R^\circ$; —$(CH_2)_{0-4}O(CH_2)_{0-1}$-pyridyl which may be substituted with $R^\circ$; —$NO_2$; —CN; —$N_3$; —$(CH_2)_{0-4}N(R^\circ)_2$; —$(CH_2)_{0-4}N(R^\circ)C(O)R^\circ$; —$N(R^\circ)C(S)R^\circ$; —$(CH_2)_{0-4}N(R^\circ)C(O)NR^\circ_2$; —$N(R^\circ)C(S)NR^\circ_2$; —$(CH_2)_{0-4}N(R^\circ)C(O)OR^\circ$; —$N(R^\circ)N(R^\circ)C(O)R^\circ$; —$N(R^\circ)N(R^\circ)C(O)NR^\circ_2$; —$N(R^\circ)N(R^\circ)C(O)OR^\circ$; —$(CH_2)_{0-4}C(O)R^\circ$; —$C(S)R^\circ$; —$(CH_2)_{0-4}C(O)OR^\circ$; —$(CH_2)_{0-4}C(O)SR^\circ$; —$(CH_2)_{0-4}C(O)OSiR^\circ_3$; —$(CH_2)_{0-4}OC(O)R^\circ$; —$OC(O)(CH_2)_{0-4}SR$—, SC(S) $SR^\circ$; —$(CH_2)_{0-4}SC(O)R^\circ$; —$(CH_2)_{0-4}C(O)NR^\circ_2$; —$C(S)NR^\circ_2$; —$C(S)SR^\circ$; —$(CH_2)_{0-4}OC(O)NR^\circ_2$; —$C(O)N(OR^\circ)R^\circ$; —$C(O)C(O)R^\circ$; —$C(O)CH_2C(O)R^\circ$; —$C(NOR^\circ)R^\circ$; —$(CH_2)_{0-4}SSR^\circ$; —$(CH_2)_{0-4}S(O)_2R^\circ$; —$(CH_2)_{0-4}S(O)_2OR^\circ$; —$(CH_2)_{0-4}OS(O)_2R^\circ$; —$S(O)_2NR^\circ_2$; —$(CH_2)_{0-4}S(O)R^\circ$; —$N(R^\circ)S(O)_2NR^\circ_2$; —$N(R^\circ)S(O)_2R^\circ$; —$N(OR^\circ)R^\circ$; —$C(NH)NR^\circ_2$; —$P(O)_2R^\circ$; —$P(O)R^\circ_2$; —$OP(O)R^\circ_2$; —$OP(O)(OR^\circ)_2$; $SiR^\circ_3$; —$(C_{1-4}$ straight or branched alkylene)O—$N(R^\circ)_2$; or —$C_{1-4}$ straight or branched alkylene)C(O)O—$N(R^\circ)_2$, wherein each $R^\circ$ may be substituted as defined below and is independently hydrogen, $C_{1-6}$ aliphatic, —$CH_2Ph$, —$O(CH_2)_{0-1}Ph$, —$CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, —$(CH_2)_{0-2}R^\bullet$, -(halo$R^\bullet$), —$(CH_2)_{0-2}OH$, —$(CH_2)_{0-2}OR'$, —$(CH_2)_{0-2}CH(OR^\bullet)_2$; —O(halo$R^\bullet$), —CN, —$N_3$, —$(CH_2)_{0-2}C(O)R^\bullet$, —$(CH_2)_{0-2}C(O)OH$, —$(CH_2)_{0-2}C(O)OR^\bullet$, —$(CH_2)_{0-2}SR^\bullet$, —$(CH_2)_{0-2}SH$, —$(CH_2)_{0-2}NH_2$, —$(CH_2)_{0-2}NHR^\bullet$, —$(CH_2)_{0-2}NR^\bullet_2$, —$NO_2$, —$SiR^\bullet_3$, —$OSiR^\bullet_3$, —$C(O)SR^\bullet$, —$(C_{1-4}$ straight or branched alkylene)C(O)O$R^\bullet$, or —$SSR^\bullet$ wherein each $R^\bullet$ is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =$NNR^*_2$, =NNHC(O)$R^*$, =NNHC(O)O$R^*$, =$NNHS(O)_2R^*$, =$NR^*$, =$NOR^*$, —$O(C(R^*_2))_{2-3}O$—, or —$S(C(R^*_2))_{2-3}S$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —$O(CR^*_2)_{2-3}O$—, wherein each independent occurrence of $R^*$ is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of $R^*$ include halogen, —$R^\bullet$, -(halo$R^\bullet$), —OH, —$OR^\bullet$, —O(halo$R^\bullet$), —CN, —C(O)OH, —C(O)O$R^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —$R^\dagger$, —$NR^\dagger_2$, —C(O)$R^\dagger$, —C(O)O$R^\dagger$, —C(O)C(O)$R^\dagger$, —C(O)$CH_2C(O)R^\dagger$, —$S(O)_2R^\dagger$, —$S(O)_2NR^\dagger_2$, —$C(S)NR^\dagger_2$, —$C(NH)NR^\dagger_2$, or —$N(R^\dagger)S(O)_2R^\dagger$; wherein each $R^\dagger$ is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of $R^\dagger$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, —$R^\bullet$, -(halo$R^\bullet$), —OH, —$OR^\bullet$, —O(halo$R^\bullet$), —CN, —C(O)OH, —C(O)O$R^\bullet$, —$NH_2$, —$NHR^\bullet$, —$NR^\bullet_2$, or —$NO_2$, wherein each $R^\bullet$ is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon-containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

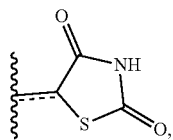

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Ingold-Prelog system can be used to assign the (R) or (S) configuration to a chiral carbon.

When the disclosed compounds contain one chiral center, the compounds exist in two enantiomeric forms. Unless specifically stated to the contrary, a disclosed compound includes both enantiomers and mixtures of enantiomers, such as the specific 50:50 mixture referred to as a racemic mixture. The enantiomers can be resolved by methods known to those skilled in the art, such as formation of diastereoisomeric salts which may be separated, for example, by crystallization (see, CRC Handbook of Optical Resolutions via Diastereomeric Salt Formation by David Kozma (CRC Press, 2001)); formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step can liberate the desired enantiomeric form. Alternatively, specific enantiomers can be synthesized by asymmetric synthesis using optically active reagents, substrates, catalysts or solvents, or by converting one enantiomer into the other by asymmetric transformation.

Designation of a specific absolute configuration at a chiral carbon in a disclosed compound is understood to mean that the designated enantiomeric form of the compounds can be provided in enantiomeric excess (e.e.). Enantiomeric excess, as used herein, is the presence of a particular enantiomer at greater than 50%, for example, greater than 60%, greater than 70%, greater than 75%, greater than 80%, greater than 85%, greater than 90%, greater than 95%, greater than 98%, or greater than 99%. In one aspect, the designated enantiomer is substantially free from the other enantiomer. For example, the "R" forms of the compounds can be substantially free from the "S" forms of the compounds and are, thus, in enantiomeric excess of the "S" forms. Conversely, "S" forms of the compounds can be substantially free of "R" forms of the compounds and are, thus, in enantiomeric excess of the "R" forms.

When a disclosed compound has two or more chiral carbons, it can have more than two optical isomers and can exist in diastereoisomeric forms. For example, when there are two chiral carbons, the compound can have up to four optical isomers and two pairs of enantiomers ((S,S)/(R,R) and (R,S)/(S,R)). The pairs of enantiomers (e.g., (S,S)/(R,R)) are mirror image stereoisomers of one another. The stereoisomers that are not mirror-images (e.g., (S,S) and (R,S)) are diastereomers. The diastereoisomeric pairs can be separated by methods known to those skilled in the art, for example chromatography or crystallization and the individual enantiomers within each pair may be separated as described above. Unless otherwise specifically excluded, a disclosed compound includes each diastereoisomer of such compounds and mixtures thereof.

The compounds according to this disclosure may form prodrugs at hydroxyl or amino functionalities using alkoxy, amino acids, etc., groups as the prodrug forming moieties. For instance, the hydroxymethyl position may form mono-, di- or triphosphates and again these phosphates can form prodrugs. Preparations of such prodrug derivatives are discussed in various literature sources (examples are: Alexander et al., J. Med. Chem. 1988, 31, 318; Aligas-Martin et al., PCT WO 2000/041531, p. 30). The nitrogen function converted in preparing these derivatives is one (or more) of the nitrogen atoms of a compound of the disclosure.

"Derivatives" of the compounds disclosed herein are pharmaceutically acceptable salts, prodrugs, deuterated forms, radioactively labeled forms, isomers, solvates and combinations thereof. The "combinations" mentioned in this context are refer to derivatives falling within at least two of the groups: pharmaceutically acceptable salts, prodrugs, deuterated forms, radioactively labeled forms, isomers, and solvates. Examples of radioactively labeled forms include compounds labeled with tritium, phosphorous-32, iodine-129, carbon-11, fluorine-18, and the like.

Compounds described herein comprise atoms in both their natural isotopic abundance and in non-natural abundance. The disclosed compounds can be isotopically labeled or isotopically substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, phosphorous, fluorine and chlorine, such as $^2$H, $^3$H, $^{13}$C, $^{14}$C, $^{15}$N, $^{18}$O, $^{17}$O, $^{35}$S, $^{18}$F and $^{36}$Cl, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules that owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

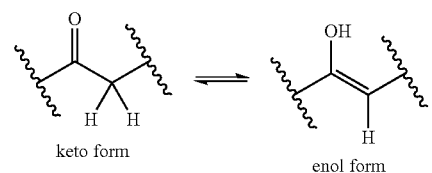

keto form        enol form

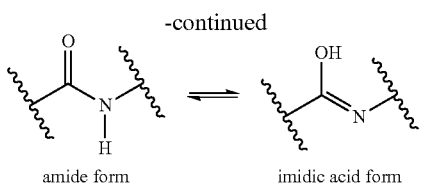

amide form ⇌ imidic acid form

Likewise, amides with an N-hydrogen can exist in an equilibrium of the amide form and the imidic acid form. As another example, pyrazoles can exist in two tautomeric forms, $N^1$-unsubstituted, 3-$A^3$ and $N^1$-unsubstituted, 5-$A^3$ as shown below.

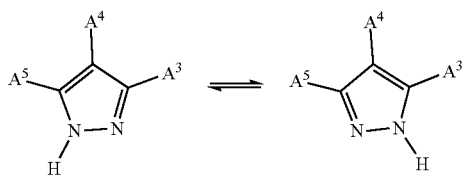

Unless stated to the contrary, the invention includes all such possible tautomers.

It is known that chemical substances form solids that are present in different states of order that are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

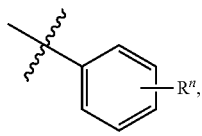

which is understood to be equivalent to a formula:

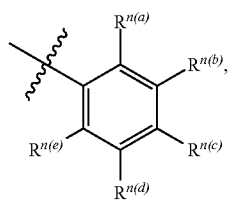

wherein n is typically an integer. That is, $R^n$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Strem Chemicals (Newburyport, Mass.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and supplemental volumes (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

B. Methods of Treating Nervous System Injury in a Subject

In one aspect, disclosed is a method of treating an injury to the nervous system in a subject, comprising administering to the subject an effective amount of disclosed compound or a pharmaceutically-acceptable thereof, as further described below, to effectively treat the injury to the nervous system in the subject. Without wishing to be bound by any theory, the described compounds can be non-peptide, therapeutically-active compounds that block Cx43 HC selectively, thereby treating Cx43 mediated effects following a traumatic injury to the nervous system.

1. Compounds

In one aspect, the compounds useful for treating an injury to the nervous system in a subject are represented by the following formula:

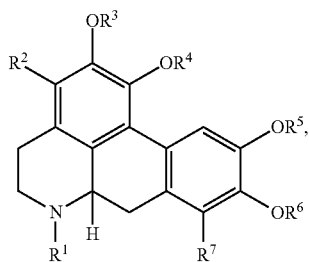

wherein $R^1$ is selected from hydrogen and C1-C4 alkyl; wherein $R^2$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^3$ and $R^4$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^3$ and $R^4$ join together to form a ring having 5-7 atoms; wherein each of $R^5$ and $R^6$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^5$ and $R^6$ join together to form a ring having 5-7 atoms; and wherein $R^7$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or a pharmaceutically-acceptable salt thereof.

In one aspect, $R^1$ is selected from hydrogen and methyl, ethyl, n-propyl, isopropyl, ethenyl, n-propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —CH$_2$NH$_2$, —CH$_2$CH$_2$NH$_2$, —CH$_2$CH$_2$CH$_2$NH$_2$, and —CH(CH$_3$)CH$_2$NH$_2$.

In a further aspect, each of $R^2$ and $R^7$ is independently selected from hydrogen, —F, —Cl, —Br, —I, —CN, —NH$_2$, —OH, —NO$_2$, methyl, ethyl, n-propyl, isopropyl, ethenyl, n-propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$.

In a still further aspect, each of $R^3$, $R^4$, $R^5$, and $R^6$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, each of $R^3$, $R^4$, $R^5$, and $R^6$ is independently selected from hydrogen, methyl, ethyl, n-propyl, isopropyl, ethenyl, n-propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$.

In another aspect, $R^3$ and $R^4$ and/or $R^5$ and $R^6$ can join together to form a ring having 5-7 atoms. Thus, for example, the compound can be represented by the formula:

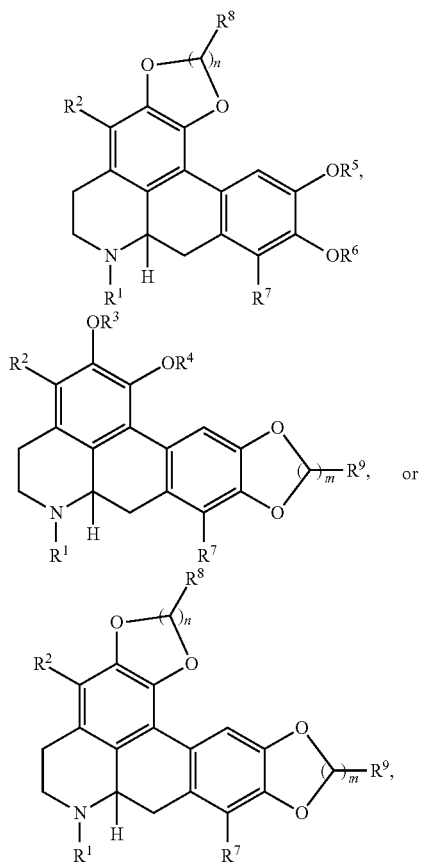

wherein each n and m is independently an integer ranging from 1-3; each of $R^8$ and $R^9$ is independently selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of $R^8$ and $R^9$ is independently selected from hydrogen, —F, —Cl, —Br, —I, —CN, —NH$_2$, —OH, —NO$_2$, methyl, ethyl, n-propyl, isopropyl, ethenyl, n-propenyl, isopropenyl, —CH$_2$F, —CH$_2$Cl, —CH$_2$CH$_2$F, —CH$_2$CH$_2$Cl, —CH$_2$CH$_2$CH$_2$F, —CH$_2$CH$_2$CH$_2$Cl, —CH(CH$_3$)CH$_2$F, —CH(CH$_3$)CH$_2$Cl, —CH$_2$CN, —CH$_2$CH$_2$CN, —CH$_2$CH$_2$CH$_2$CN, —CH(CH$_3$)CH$_2$CN, —CH$_2$OH, —CH$_2$CH$_2$OH, —CH$_2$CH$_2$CH$_2$OH, —CH(CH$_3$)CH$_2$OH, —OCF$_3$, —OCH$_2$CF$_3$, —OCH$_2$CH$_2$CF$_3$, —OCH(CH$_3$)CF$_3$, —OCH$_3$, —OCH$_2$CH$_3$, —OCH$_2$CH$_2$CH$_3$, —OCH(CH$_3$)CH$_3$, —NHCH$_3$, —NHCH$_2$CH$_3$, —NHCH$_2$CH$_2$CH$_3$, —NHCH(CH$_3$)CH$_3$, —N(CH$_3$)$_2$, —N(CH$_2$CH$_3$)$_2$, —N(CH$_2$CH$_2$CH$_3$)$_2$, —N(CH(CH$_3$)CH$_3$)$_2$, —N(CH$_3$)(CH$_2$CH$_3$), —CH$_2$NH$_2$, —CH$_2$CH$_2$NH$_2$, —CH$_2$CH$_2$CH$_2$NH$_2$, and —CH(CH$_3$)CH$_2$NH$_2$.

In one aspect, each of $R^1$, $R^4$, and $R^5$ is independently selected from hydrogen, methyl, ethyl, and propyl; each of $R^2$ and $R^7$ is independently selected from hydrogen and halogen; and each of $R^3$ and $R^6$ is hydrogen.

In a further aspect, each of $R^1$, $R^4$, and $R^5$ is methyl; each of $R^2$ and $R^7$ is independently selected from hydrogen and halogen; and each of $R^3$ and $R^6$ is hydrogen.

In a still further aspect, each of $R^1$, $R^4$, and $R^5$ is independently selected from hydrogen, methyl, ethyl, and propyl; and each of $R^2$, $R^3$, $R^6$, and $R^7$ is hydrogen.

Non-limiting examples of compounds having hydrogen or C1-C4 substitutions at $R^1$ include the following. The C1-C4 substituents at $R^*$, when present, can be optionally substituted as described above.
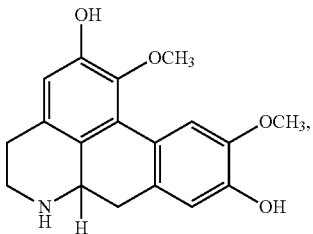
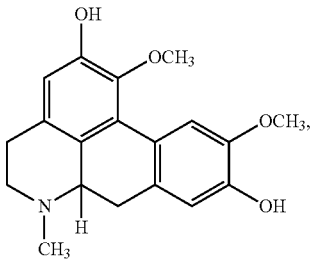
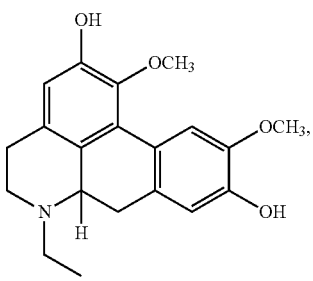
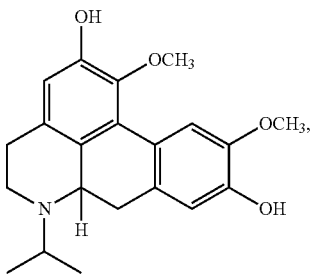
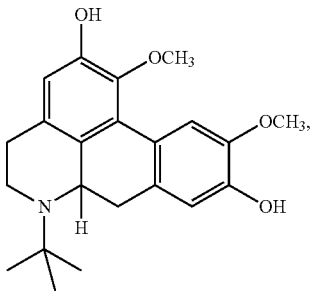
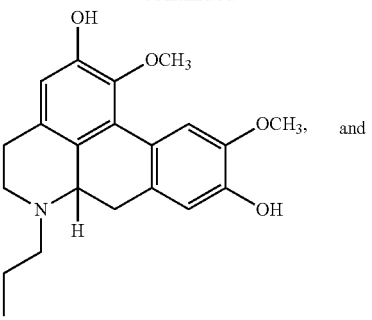
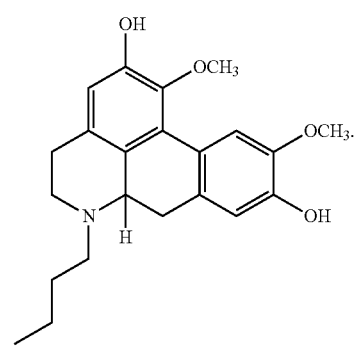 [SMILES: CCCCN1CCc2cc(O)c(OC)c3c2C1Cc1cc(O)c(OC)cc1-3]
Non-limiting examples of compounds having substitutions at $R^2$ and/or $R^7$ include the following:
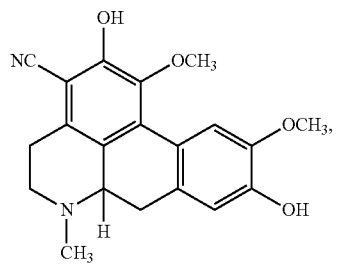
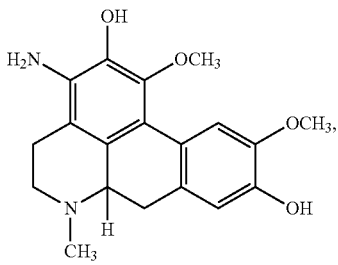
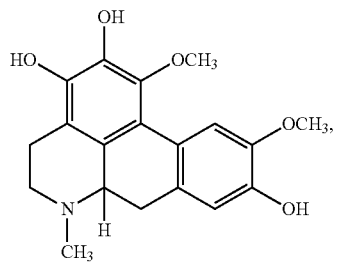

-continued
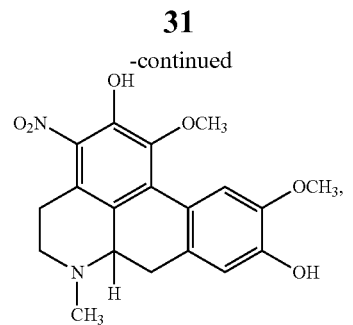
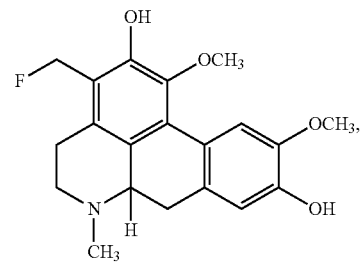
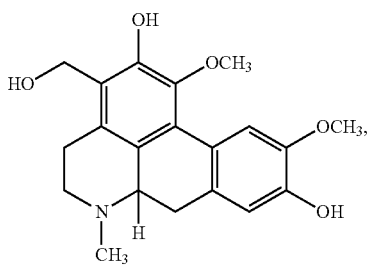
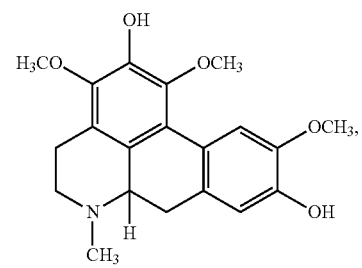
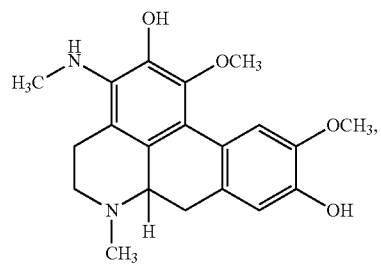
-continued
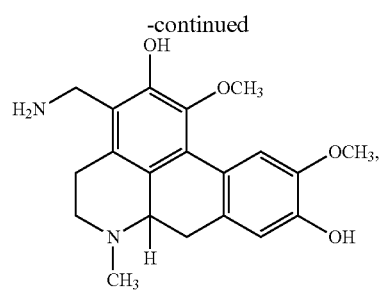
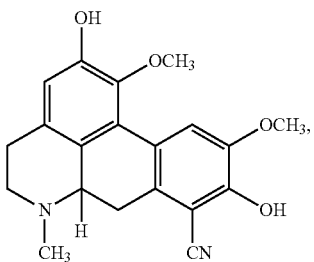
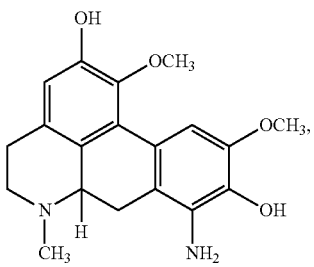
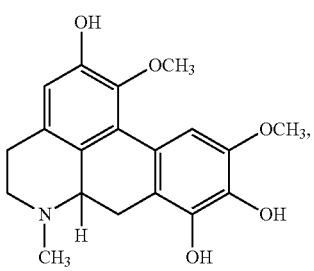
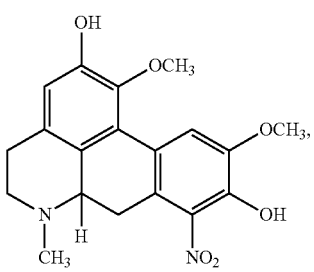
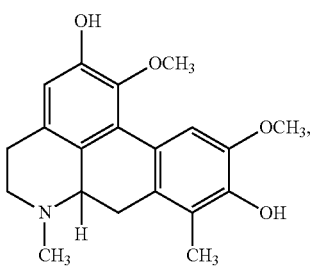

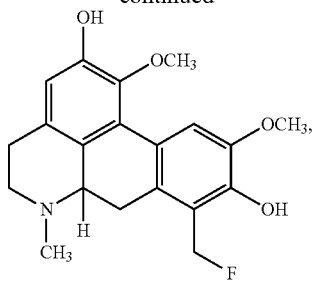
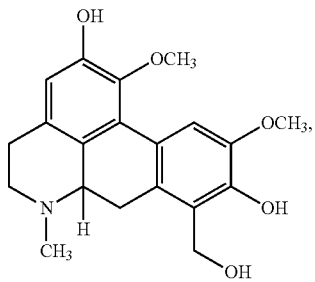
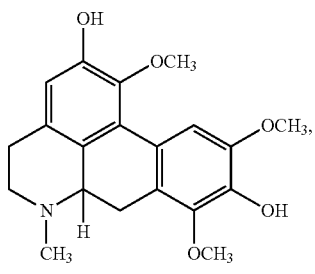
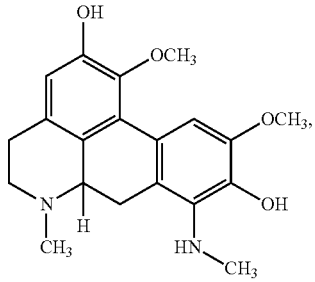
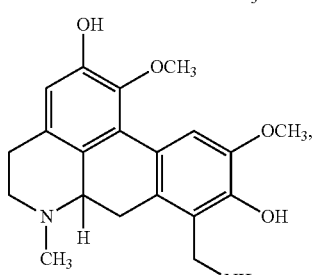
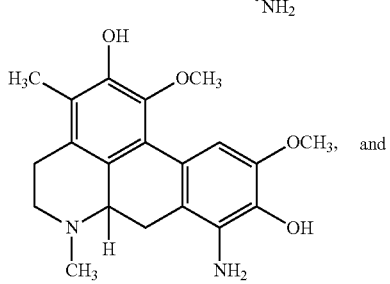
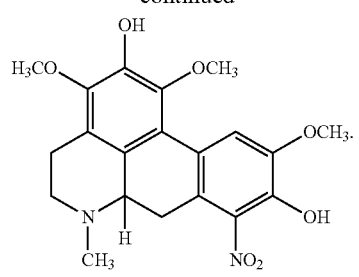
Non-limiting examples of compounds having a halogen at $R^2$ and/or $R^7$ include the following:
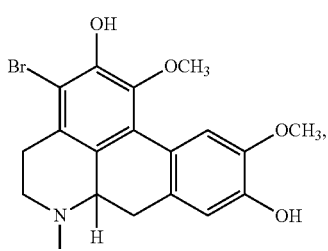
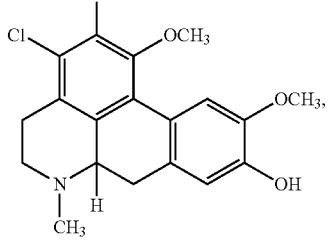
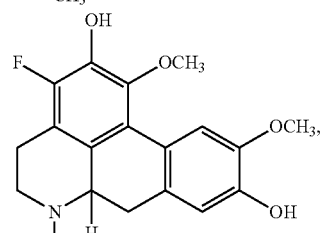
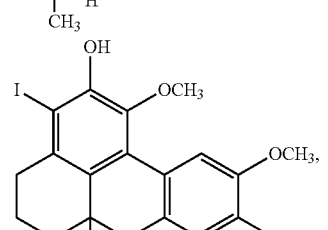
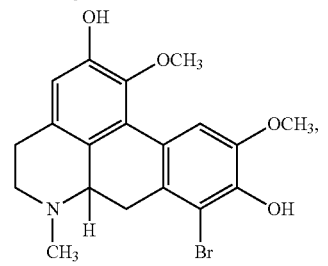

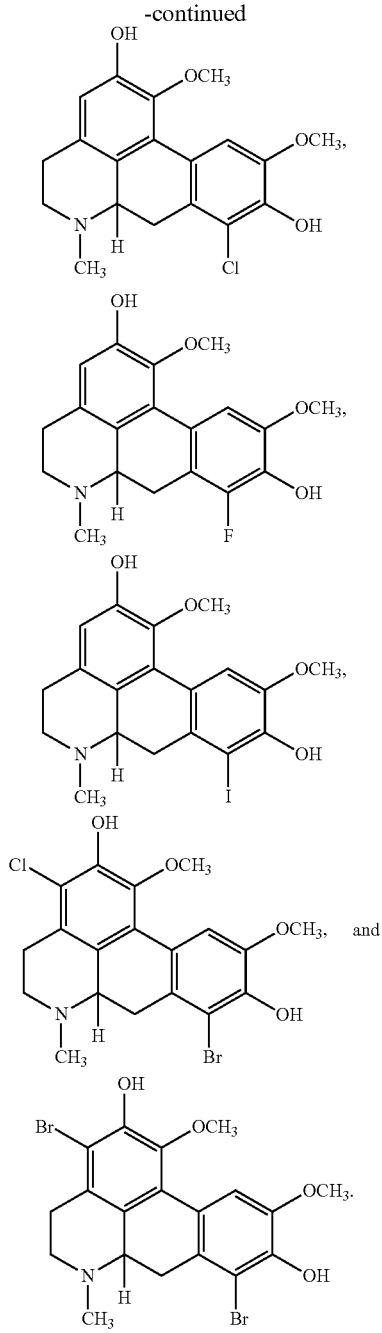
Non-limiting examples of compounds substituted at R³-R⁶ include the following:
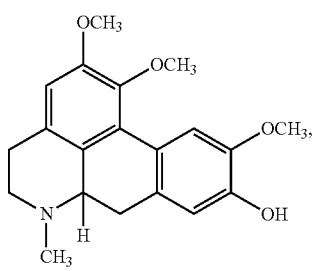
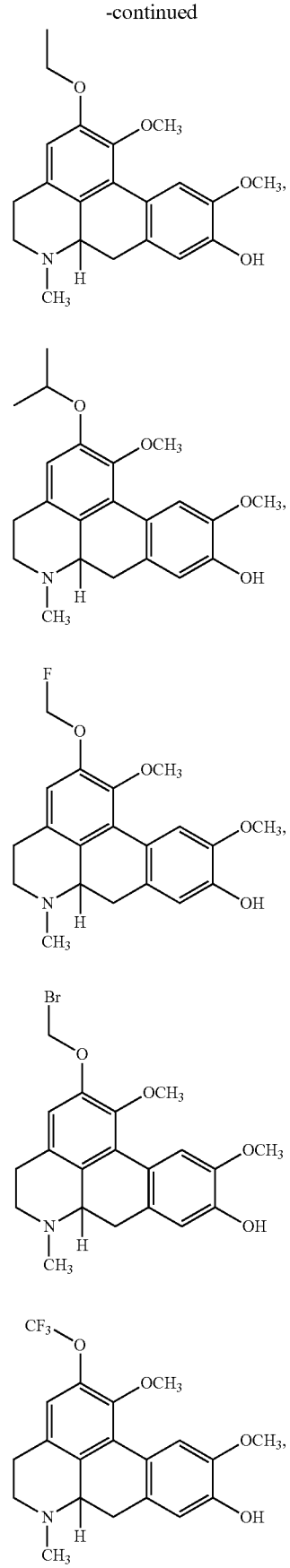

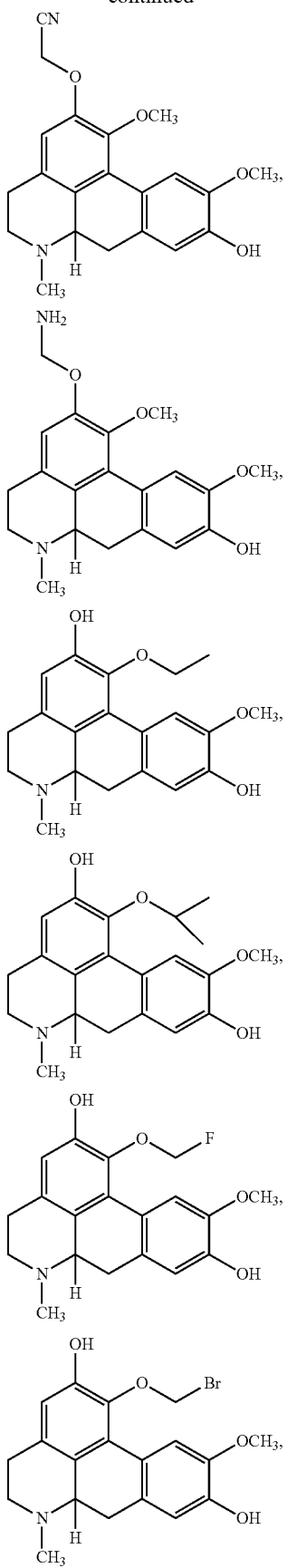
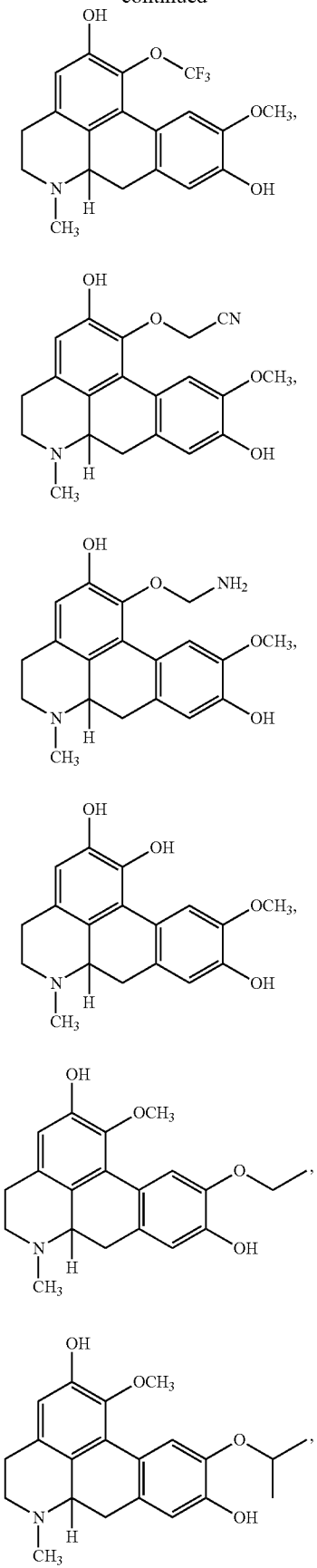

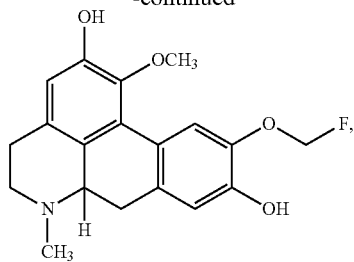
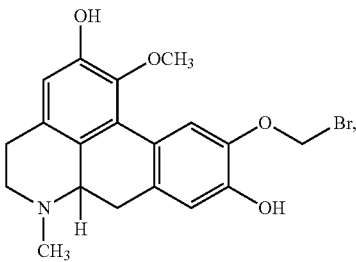
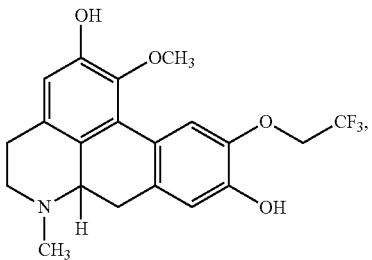
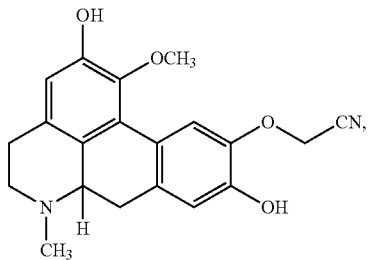
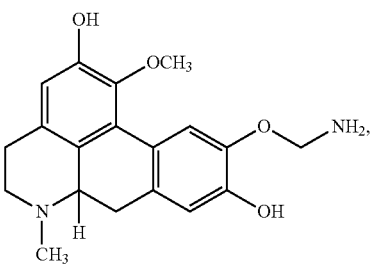
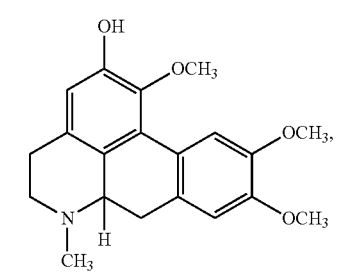
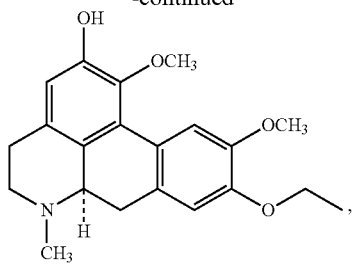
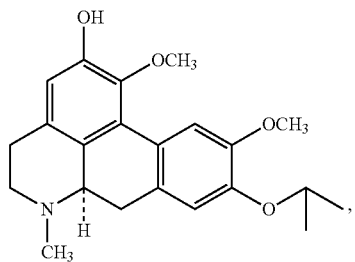
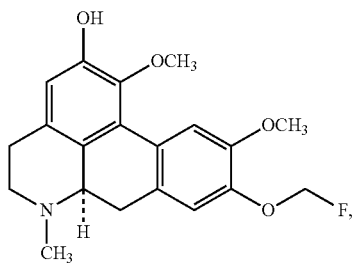
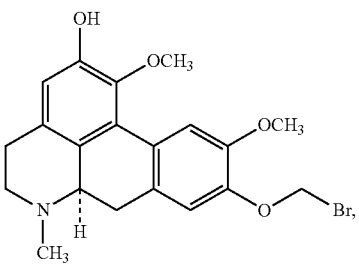
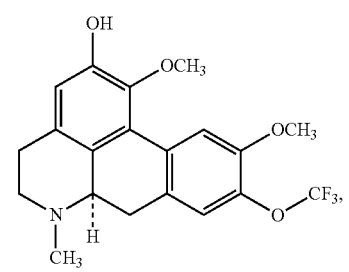
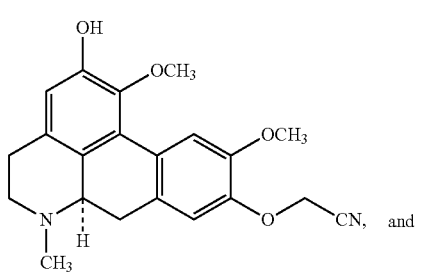

-continued

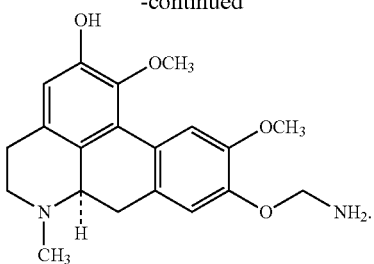

According to one aspect, the compound is represented by the formula:

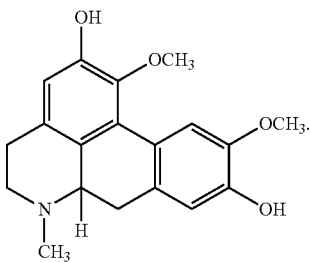 [SMILES: COc1cc2c(cc1O)CC1c3c(cc(O)c(OC)c3-2)CCN1C]

The compound shown above corresponds to a racemic mixture of boldine. Boldine is a naturally-occurring alkaloid present in the leaves and bark of Boldo (*Peumus boldus* Molina), a tree native to the central region of Chile, among other plants.

In various aspects, the compounds have at least one chiral center and can be substantially free of other isomers (e.g., as a pure or substantially pure optical isomer having a specified activity), or may be admixed, for example, with racemates or other stereoisomers. In one aspect, the compound can be substantially enantiomerically pure. For example, the S enantiomer of boldine can be substantially free of or separated from the R enantiomer of boldine. Similarly, for example, the R enantiomer of boldine can be substantially free of or separated from the S enantiomer of boldine. In one aspect, the compound can be about 80% enantiomerically pure, about 85% enantiomerically pure, about 90% enantiomerically pure, about 91% enantiomerically pure, about 92% enantiomerically pure, about 93% enantiomerically pure, about 94% enantiomerically pure, about 95% enantiomerically pure, about 96% enantiomerically pure, about 97% enantiomerically pure, about 98% enantiomerically pure, about 99% enantiomerically pure, or about 100% enantiomerically pure.

In one exemplary aspect, the compound is represented by the following formula:

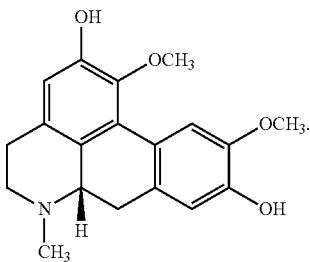 [SMILES: COc1cc2c(cc1O)C[C@H]1c3c(cc(O)c(OC)c3-2)CCN1C]

The compound shown above is the S enantiomer of boldine (also known by the IUPAC name, (S)-1,10-dimethoxy-6-methyl-5,6,6a,7-tetrahydro-4H-dibenzo[de,g]quinoline-2,9-diol). S-boldine, when present, can be substantially free of other isomers (e.g., as a pure or substantially pure optical isomer having a specified activity), or may be admixed, for example, with racemates or other stereoisomers. In one aspect, S-boldine, when present, can be about 80% enantiomerically pure, about 85% enantiomerically pure, about 90% enantiomerically pure, about 91% enantiomerically pure, about 92% enantiomerically pure, about 93% enantiomerically pure, about 94% enantiomerically pure, about 95% enantiomerically pure, about 96% enantiomerically pure, about 97% enantiomerically pure, about 98% enantiomerically pure, about 99% enantiomerically pure, or about 100% enantiomerically pure.

The compounds can be administered to a subject as a pharmaceutically-acceptable salt. Non-limiting examples of pharmaceutically-acceptable salts are mineral acid (hydrochloric acid, hydrobromic acid, phosphoric acid, and the like) salts, organic acid (acetic acid, propionic acid, glutamic acid, citric acid and the like) salts, and quaternary ammonium (methyl iodide, ethyl iodide, and the like) salts. Other non-limiting examples include, but are not limited to, sulfate, citrate, acetate, oxalate, chloride, bromide, iodide, nitrate, bisulfate, phosphate, acid phosphate, phosphonic acid, isonicotinate, lactate, salicylate, citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Still other salts include, but are not limited to, salts with inorganic bases including alkali metal salts such as sodium salts, and potassium salts; alkaline earth metal salts such as calcium salts, and magnesium salts; aluminum salts; and ammonium salts. Other salts with organic bases include salts with diethylamine, diethanolamine, meglumine, and N,N'-dibenzylethylenediamine. It is understood that the pharmaceutically acceptable salts are non toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutically-acceptable salts of the compounds can be salts formed with bases, namely cationic salts such as alkali and alkaline earth metal salts, such as sodium, lithium, potassium, calcium, magnesium, as well as ammonium salts, such as ammonium, trimethyl-ammonium, diethylammonium, and tris-(hydroxymethyl)-methyl-ammonium salts. Similarly, acid addition salts, such as mineral acids, organic carboxylic and organic sulfonic acids, e.g., hydrochloric acid, methanesulfonic acid, maleic acid, are also contemplated. Neutral forms of boldine and its analogs can be regenerated by contacting the salt with a base or acid and isolating the parent compound in a conventional manner.

In one aspect, the compound used for treating an injury to the nervous system in a subject is 5-boldine hydrochloride. 5-boldine hydrochloride can be prepared from Boldo's bark, as described in A. Urzua and P. Acura, "Alkaloids from the bar of *Peumus boldus*," Fitoterapia, vol. 54, no. 4, pp. 175-177, 1983, which is incorporated herein by reference.

2. Methods of Making the Compounds

In some aspects, the compounds can be obtained from a natural source, e.g., a plant or component thereof that naturally produces certain alkaloids such as those described herein. In a further aspect, the compounds can be prepared according to the oxidative coupling reaction shown in Scheme 1.

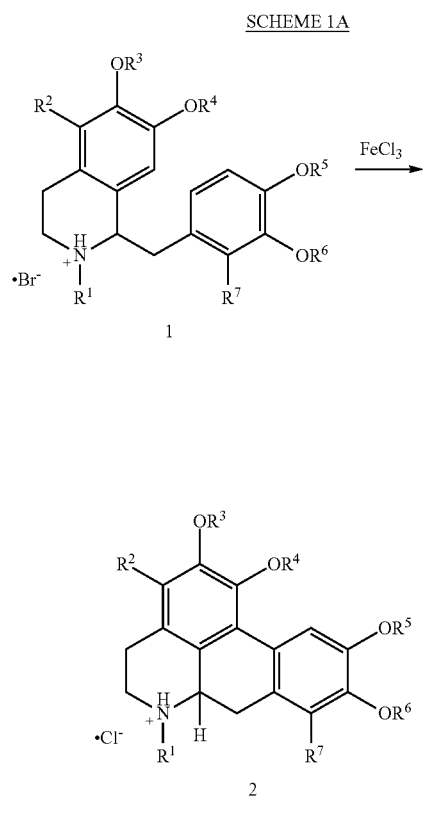

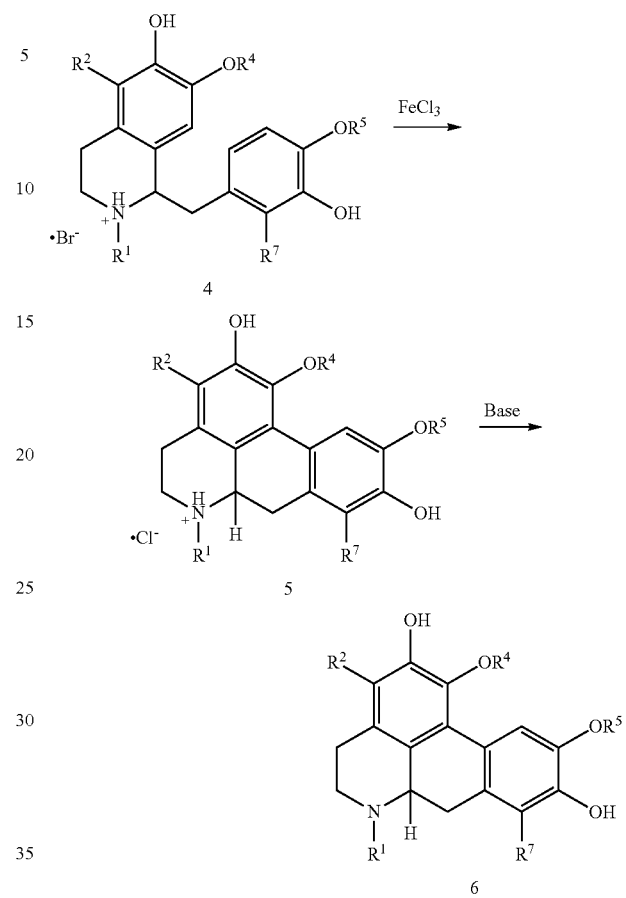

Precursor compounds (1) can be dissolved in a suitable solvent such as ethanol, water, or a combination thereof, and subjected to oxidative coupling using a strong Lewis acid such as ferric chloride ($FeCl_3$) with a suitable acid such as hydrochloric acid. Following the coupling reaction, the resulting salts (2) can be converted to the neutral compounds (3) if desired using a suitable base.

In a further aspect, an oxidative coupling reaction can be used on compounds (4), which have at least one unsubstituted phenolic functional group. Salts (5) can be reduced to neutral form (6) using a suitable base. The unsubstituted phenolic groups can be further substituted as desired.

According to one aspect, compounds (6) can be further substituted at one or more phenolic hydroxyl groups according to Scheme 2. A suitable quaternary ammonium salt such as 7 shown below can be dissolved in a suitable solvent such as methanol with a suitable base such as potassium hydroxide to give the corresponding substituted compounds (8).

-continued

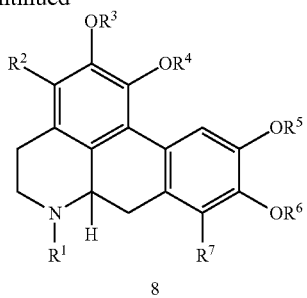

8

According to one aspect, compounds in which $R^3$ and $R^4$ and/or $R^5$ and $R^6$ join together to form a ring having 5-7 atoms can be prepared according to methods known in the art. In one aspect, such compounds can be prepared by nucleophilic substitution reactions such as the one shown below in Scheme 3.

SCHEME 3

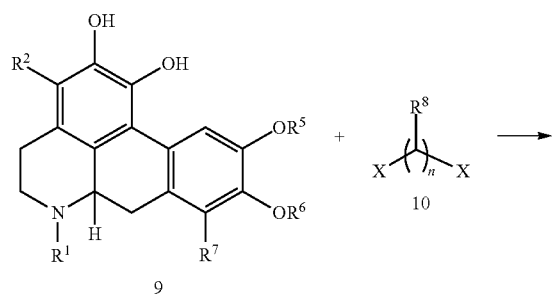

9

10

11

In general, the reaction shown in Scheme 3 can be accomplished with a suitable weak base such as potassium carbonate, with the addition of potassium iodide, in a suitable solvent such as dimethylformamide. According to one aspect, the reaction shown above can be carried out at a suitable temperature, e.g., 105-120° C., for a suitable time, e.g., 1-12 hours. Other methods of preparing compounds in which $R^3$ and $R^4$ and/or $R^5$ and $R^6$ join together to form a ring having 5-7 atoms will be recognized by those skilled in the art.

In a further aspect, compounds with halogen substitutions at $R^2$ and/or $R^7$ can be prepared according to methods known in the art, such as the exemplary reaction Scheme 4.

SCHEME 4

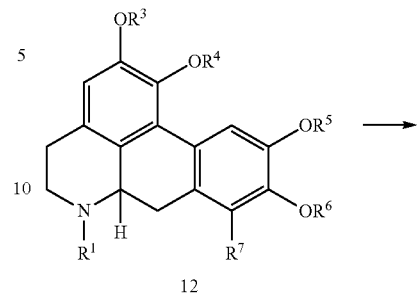

12

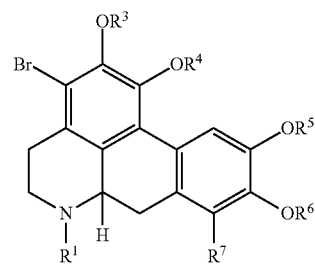

13

Compounds of type (12) can be substituted with bromine, for example, using trifluoroacetic acid and a suitable reagent such as N-Bromosuccinimide for a suitable time such as 1-3 hours at room temperature to give compounds of type (13). Scheme 4 can be tailored as one of skill will appreciate to prepare various halogen substitution patterns on the aromatic rings.

3. Pharmaceutically-Acceptable Carriers and Dosage Forms

In various aspects, the compounds can be administered to a subject as a composition or formulation comprising a pharmaceutically-acceptable carrier. Non-limiting examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants.

Pharmaceutically-acceptable carries can also comprise adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms can be made by forming microencapsule matrices of the compounds in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations can also be prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

In some aspects, the pharmaceutically-acceptable carrier can include an excipient. Suitable excipients include, without limitation, saccharides, for example, glucose, lactose, or sucrose, mannitol, or sorbitol, cellulose derivatives, and/or calcium phosphate, for example, tricalcium phosphate or acidic calcium phosphate.

In further aspects, the pharmaceutically-acceptable carrier can include a binder. Suitable binders include, without limitation, tare compounds such as starch paste, for example, corn, wheat, rice, and potato starch, gelatin, tragacanth, methylcellulose, hydroxypropyl methylcellulose, carboxymethylcellulose, and/or polyvinylpyrrolidone. In still further aspects, there can be a disintegrating agent, such as the aforementioned starches and carboxymethyl starch, crosslinked polyvinylpyrrolidone, agar, or alginic acid or a salt thereof, such as sodium alginate.

In some aspects, the pharmaceutically-acceptable carrier can include an additive. Examples of additives include, but are not limited to, diluents, buffers, binders, surface-active agents, lubricants, humectants, pH adjusting agents, preservatives (including anti-oxidants), emulsifiers, occlusive agents, opacifiers, antioxidants, colorants, flavoring agents, gelling agents, thickening agents, stabilizers, and surfactants, among others. Thus, in various further aspects, the additive is vitamin E, gum acacia, citric acid, *stevia* extract powder, Luo Han Gou, Monoammonium Glycyrhizinate, Ammonium Glycyrrhizinate, honey, or combinations thereof. In a still further aspect, the additive is a flavoring agent, a binder, a disintegrant, a bulking agent, or silica. In a further aspect, the additive can include flowability-control agents and lubricants, such as silicon dioxide, talc, stearic acid and salts thereof, such as magnesium stearate or calcium stearate, and/or propylene glycol.

In various aspects, when the compounds are formulated for oral use, such as for example, a tablet, pill, or capsule, the composition can include a coating layer that is resistant to gastric acid. Such a layer, in various aspects, can include a concentrated solution of saccharides that can comprise gum arabic, talc, polyvinylpyrrolidone, polyethylene glycol, and/or titanium dioxide, and suitable organic solvents or salts thereof.

Dosage forms can comprise the compounds or a pharmaceutically-acceptable salt thereof, together in combination with a pharmaceutically acceptable excipient, such as a preservative, buffer, saline, or phosphate buffered saline. Dosage forms can be made using conventional pharmaceutical manufacturing and compounding techniques. Dosage forms can comprise inorganic or organic buffers (e.g., sodium or potassium salts of phosphate, carbonate, acetate, or citrate) and pH adjustment agents (e.g., hydrochloric acid, sodium or potassium hydroxide, salts of citrate or acetate, amino acids and their salts) antioxidants (e.g., ascorbic acid, alpha-tocopherol), surfactants (e.g., polysorbate 20, polysorbate 80, polyoxyethylene9-10 nonyl phenol, sodium desoxycholate), solution and/or cryo/lyo stabilizers (e.g., sucrose, lactose, mannitol, trehalose), osmotic adjustment agents (e.g., salts or sugars), antibacterial agents (e.g., benzoic acid, phenol, gentamicin), antifoaming agents (e.g., polydimethylsilozone), preservatives (e.g., thimerosal, 2-phenoxyethanol, EDTA), polymeric stabilizers and viscosity-adjustment agents (e.g., polyvinylpyrrolidone, poloxamer 488, carboxymethylcellulose) and co-solvents (e.g., glycerol, polyethylene glycol, ethanol). A dosage form formulated for injectable use can have a disclosed composition or a product of a disclosed method of making, suspended in sterile saline solution for injection together with a preservative.

4. Treatment Methods

In one aspect, the compounds can be administered to a subject having an injury to the nervous system. According to one aspect, the injury to the nervous system is a central nervous system injury or a peripheral nervous system injury. In a further aspect, the injury to the nervous system is a spinal cord injury (SCI), spinal cord contusion, nerve crush injury, or traumatic brain injury (TBI). In a still further aspect, a symptom of the injury to the nervous system is neuropathic pain, loss of voluntary muscle control, loss of locomotor function, or a combination thereof.

In some aspects, the compounds, when administered to the subject in a therapeutically effective amount, can be sufficient to cause a detectable improvement in, or a reduction in the progression of, one or more of the following symptoms of the injury to the nervous system: neuropathic pain, loss of neuroplasticity, loss of voluntary muscle control, loss or impairment of locomotor function, loss or impairment of sensory function, or a combination thereof.

For example, when the injury to the nervous system is a spinal cord injury (SCI), the compounds can improve nervous system dysfunction caused by trauma to the cervical, thoracic, lumbar or sacral segments of the spinal cord, including without limitation dysfunction caused by trauma to one or more of dermatomes C1, C2, C3, C4, C5, C6, C7, T1, T2, T3, T4, T5, T6, T7, T8, T9, T10, T11, T12, L1, L2, L3, L4 or L5.

Similarly, in some aspects, the compounds can improve nervous system dysfunction resulting from traumatic brain injury (TBI). In various aspects, the TBI can be an injury to the frontal lobe, parietal lobe, occipital lobe, temporal lobe, brain stem, or cerebellum. In some aspects, the TBI is a mild TBI. In a further aspect, the TBI is a moderate to severe TBI. The compounds can, in various aspects, cause a detectable improvement in, or a reduction in the progression of, one or more of the following symptoms of TBI: headache, memory problems, attention deficits, mood swings and frustration, fatigue, visual disturbances, memory loss, poor attention/concentration, sleep disturbances, dizziness/loss of balance, irritability, emotional disturbances, feelings of depression, seizures, nausea, loss of smell, sensitivity to light and sounds, mood changes, getting lost or confused, or slowness in thinking.

In various aspects, the method comprises administering to the subject having an injury to the nervous system an effective amount of a compound represented by the following formula:

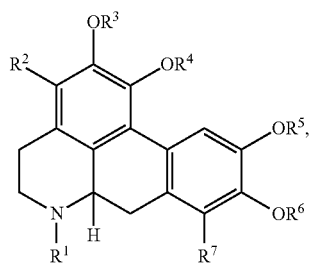

wherein R¹ is selected from hydrogen and C1-C4 alkyl; wherein R² is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of R³ and R⁴ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R³ and R⁴ join together to form a ring having 5-7 atoms; wherein each of R⁵ and R⁶ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein R⁵ and R⁶ join together to form a ring having 5-7 atoms; and wherein R⁷ is selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or a pharmaceutically-acceptable salt thereof.

In one aspect, R¹ is selected from hydrogen and methyl, ethyl, n-propyl, isopropyl, ethenyl, n-propenyl, isopropenyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —CH₂CN, —CH₂CH₂CN, —CH₂CH₂CH₂CN, —CH(CH₃)CH₂CN, —CH₂OH, —CH₂CH₂OH, —CH₂CH₂CH₂OH, —CH(CH₃)CH₂OH, —CH₂NH₂, —CH₂CH₂NH₂, —CH₂CH₂CH₂NH₂, and —CH(CH₃)CH₂NH₂.

In a further aspect, each of R² and R⁷ is independently selected from hydrogen, —F, —Cl, —Br, —I, —CN, —NH₂, —OH, —NO₂, methyl, ethyl, n-propyl, isopropyl, ethenyl, n-propenyl, isopropenyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —CH₂CN, —CH₂CH₂CN, —CH₂CH₂CH₂CN, —CH(CH₃)CH₂CN, —CH₂OH, —CH₂CH₂OH, —CH₂CH₂CH₂OH, —CH(CH₃)CH₂OH, —OCF₃, —OCH₂CF₃, —OCH₂CH₂CF₃, —OCH(CH₃)CF₃, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), —CH₂NH₂, —CH₂CH₂NH₂, —CH₂CH₂CH₂NH₂, and —CH(CH₃)CH₂NH₂.

In a still further aspect, each of R³, R⁴, R⁵, and R⁶ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a still further aspect, each of R³, R⁴, R⁵, and R⁶ is independently selected from hydrogen, methyl, ethyl, n-propyl, isopropyl, ethenyl, n-propenyl, isopropenyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —CH₂CN, —CH₂CH₂CN, —CH₂CH₂CH₂CN, —CH(CH₃)CH₂CN, —CH₂OH, —CH₂CH₂OH, —CH₂CH₂CH₂OH, —CH(CH₃)CH₂OH, —OCF₃, —OCH₂CF₃, —OCH₂CH₂CF₃, —OCH(CH₃)CF₃, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), —CH₂NH₂, —CH₂CH₂NH₂, —CH₂CH₂CH₂NH₂, and —CH(CH₃)CH₂NH₂.

In another aspect, R³ and R⁴ and/or R⁵ and R⁶ can join together to form a ring having 5-7 atoms. Thus, for example, the compound can be represented by the formula:

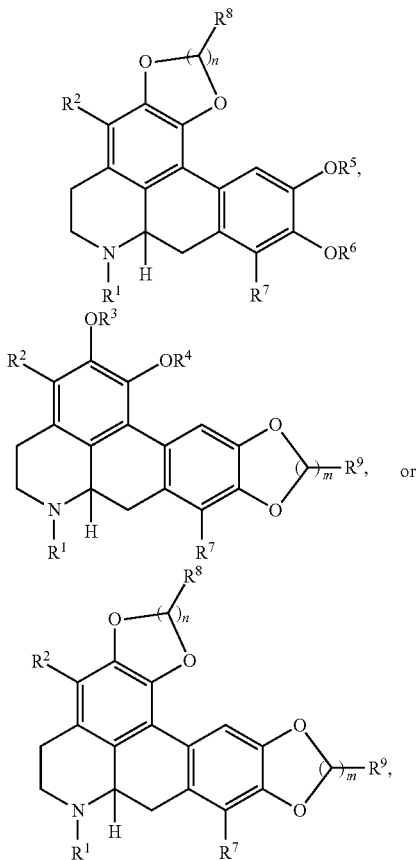

wherein each n and m is independently an integer ranging from 1-3; each of R⁸ and R⁹ is independently selected from hydrogen, halogen, —CN, —NH₂, —OH, —NO₂, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl. In a further aspect, each of R⁸ and R⁹ is independently selected from hydrogen, —F, —Cl, —Br, —I, —CN, —NH₂, —OH, —NO₂, methyl, ethyl, n-propyl, isopropyl, ethenyl, n-propenyl, isopropenyl, —CH₂F, —CH₂Cl, —CH₂CH₂F, —CH₂CH₂Cl, —CH₂CH₂CH₂F, —CH₂CH₂CH₂Cl, —CH(CH₃)CH₂F, —CH(CH₃)CH₂Cl, —CH₂CN, —CH₂CH₂CN, —CH₂CH₂CH₂CN, —CH(CH₃)CH₂CN, —CH₂OH, —CH₂CH₂OH, —CH₂CH₂CH₂OH, —CH(CH₃)CH₂OH, —OCF₃, —OCH₂CF₃, —OCH₂CH₂CF₃, —OCH(CH₃)CF₃, —OCH₃, —OCH₂CH₃, —OCH₂CH₂CH₃, —OCH(CH₃)CH₃, —NHCH₃, —NHCH₂CH₃, —NHCH₂CH₂CH₃, —NHCH(CH₃)CH₃, —N(CH₃)₂, —N(CH₂CH₃)₂, —N(CH₂CH₂CH₃)₂, —N(CH(CH₃)CH₃)₂, —N(CH₃)(CH₂CH₃), —CH₂NH₂, —CH₂CH₂NH₂, —CH₂CH₂CH₂NH₂, and —CH(CH₃)CH₂NH₂.

In one aspect, each of R¹, R⁴, and R⁵ is independently selected from hydrogen, methyl, ethyl, and propyl; each of R² and R⁷ is independently selected from hydrogen and halogen; and each of R³ and R⁶ is hydrogen.

In a further aspect, each of $R^1$, $R^4$, and $R^5$ is methyl; each of $R^2$ and $R^7$ is independently selected from hydrogen and halogen; and each of $R^3$ and $R^6$ is hydrogen.

In a still further aspect, each of $R^1$, $R^4$, and $R^5$ is independently selected from hydrogen, methyl, ethyl, and propyl; and each of $R^2$, $R^3$, $R^6$, and $R^7$ is hydrogen.

Non-limiting examples of compounds that can be administered to the subject, which have hydrogen or C1-C4 substitutions at $R^1$ include the following. The C1-C4 substituents at $R^*$, when present, can be optionally substituted as described above.

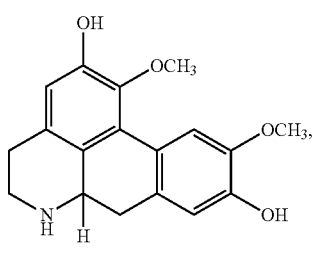

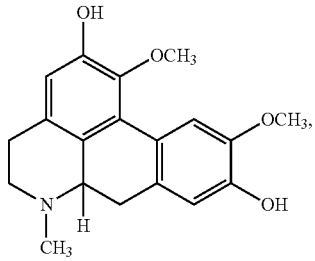

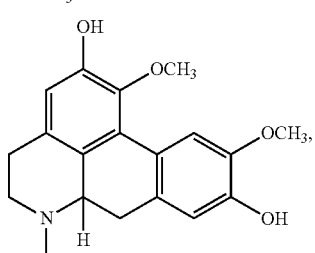

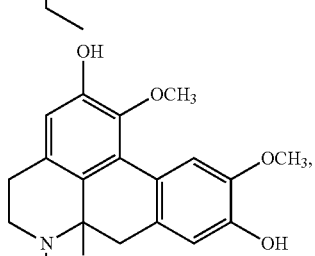

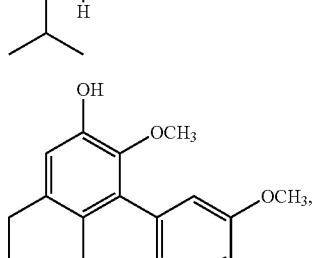

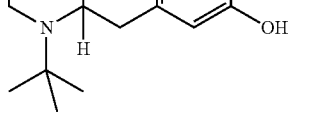

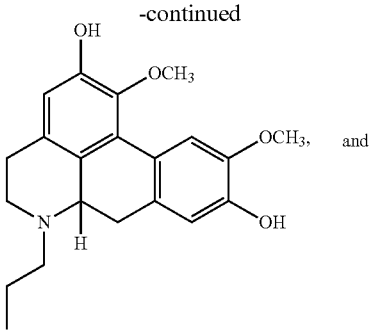

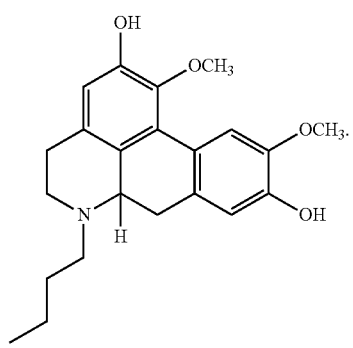 [SMILES: CCCCN1CCc2cc(O)c(OC)c3c2C1Cc1cc(O)c(OC)cc1-3]

Non-limiting examples of compounds suitable for administration to a subject, which have substitutions at $R^2$ and/or $R^7$ include the following:

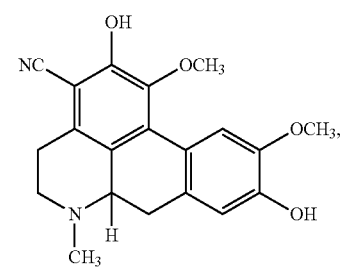

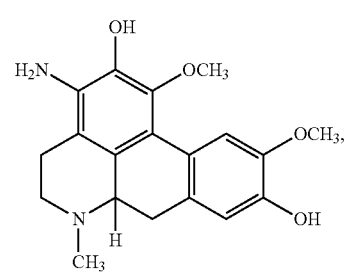

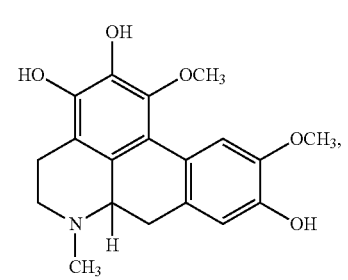

-continued
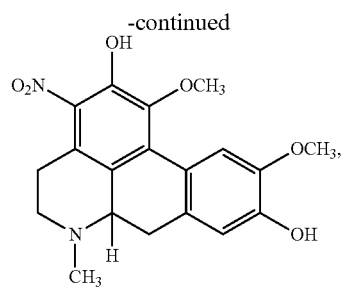
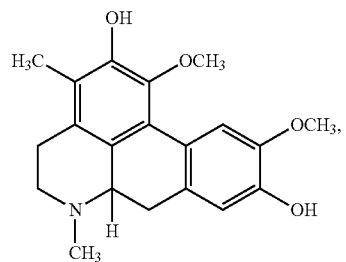
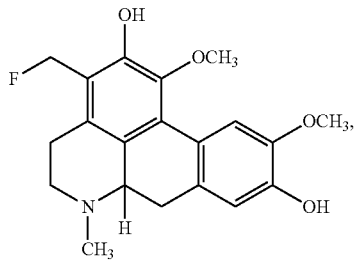
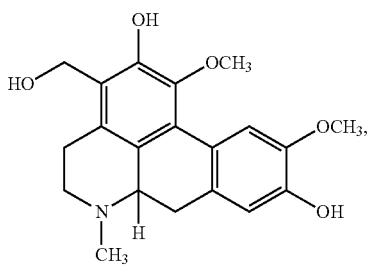
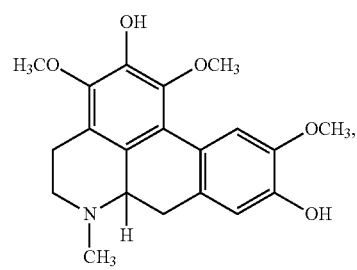
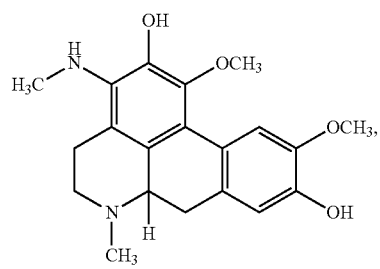
-continued
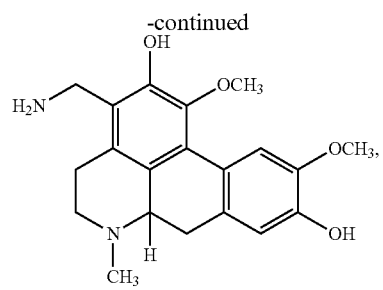
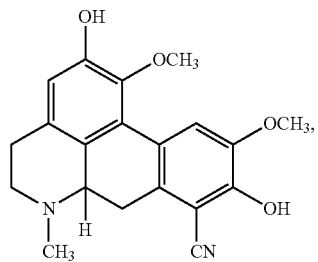
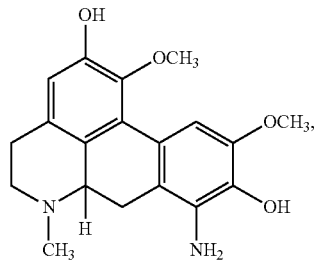
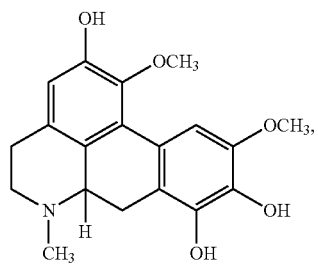
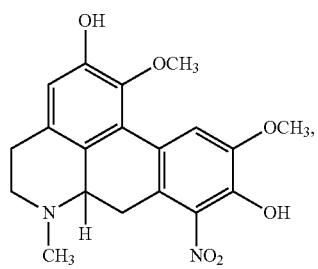
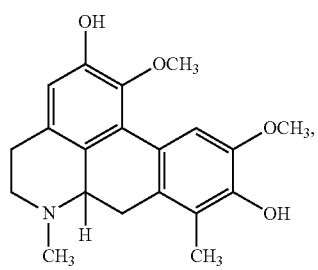

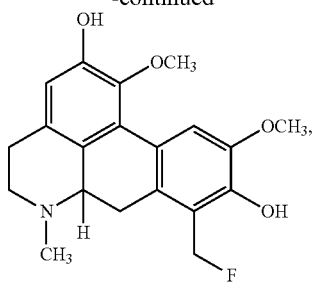
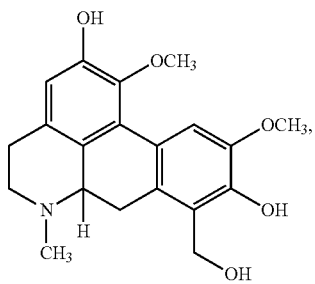
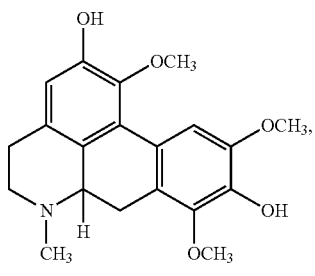
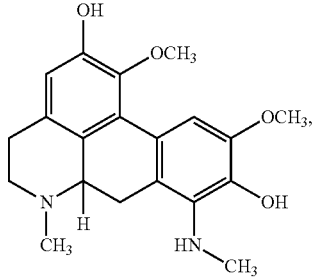
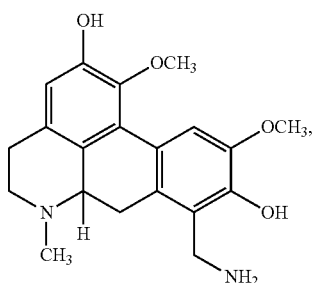
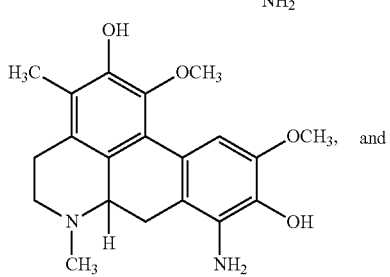
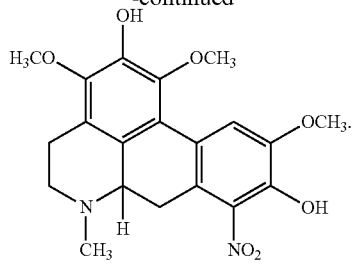
Non-limiting examples of compounds suitable for administration to a subject, which have a halogen at $R^2$ and/or $R^7$ include the following:
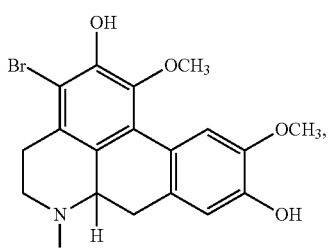
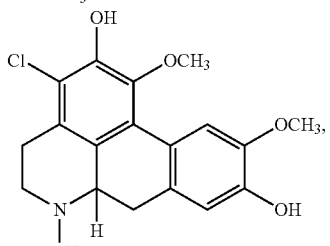
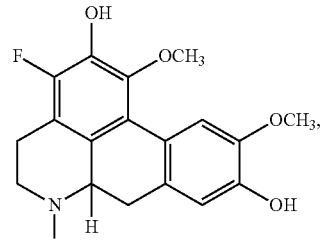
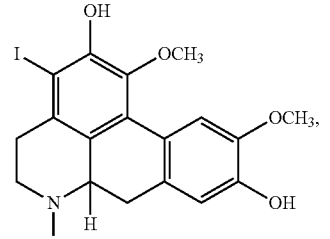
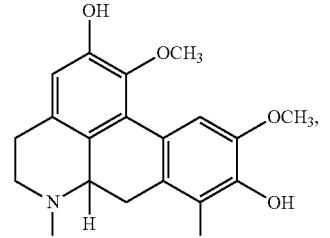

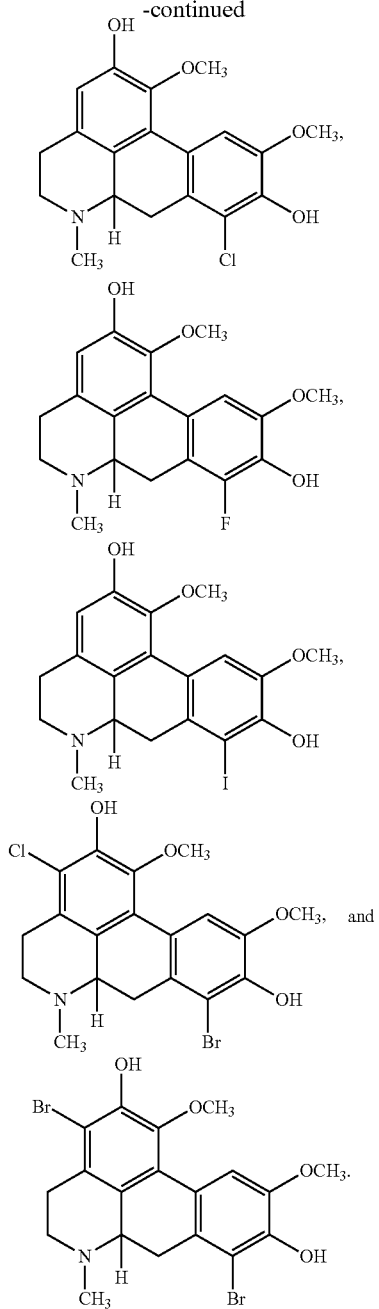
Non-limiting examples of compounds substituted at $R^3$-$R^6$ which are suitable for administration to a subject include the following:
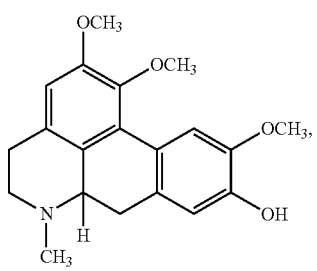 [SMILES: COc1cc2c(cc1O)CC1c3c(cc(O)c(OC)c3-2)CCN1C]
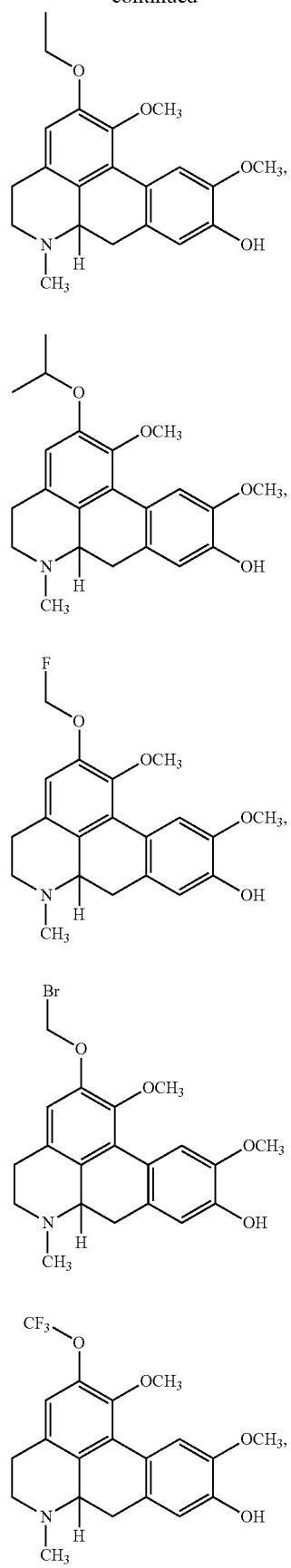

-continued
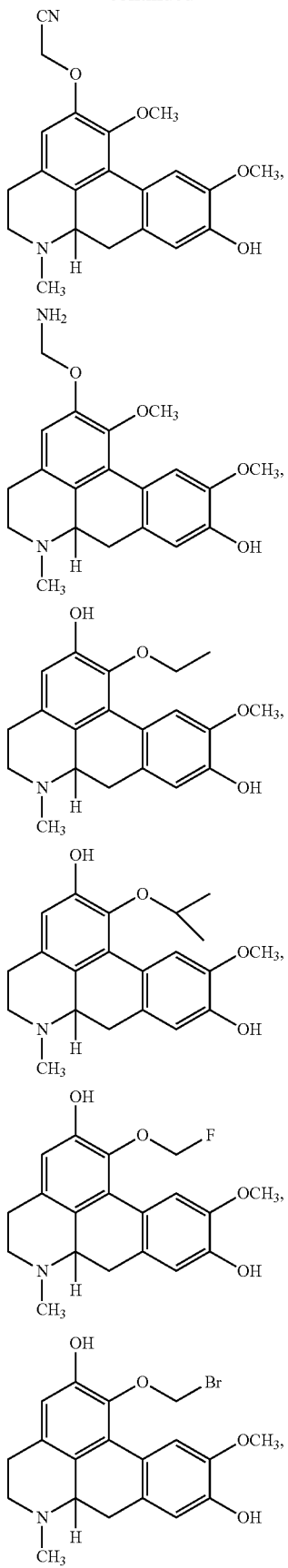
-continued
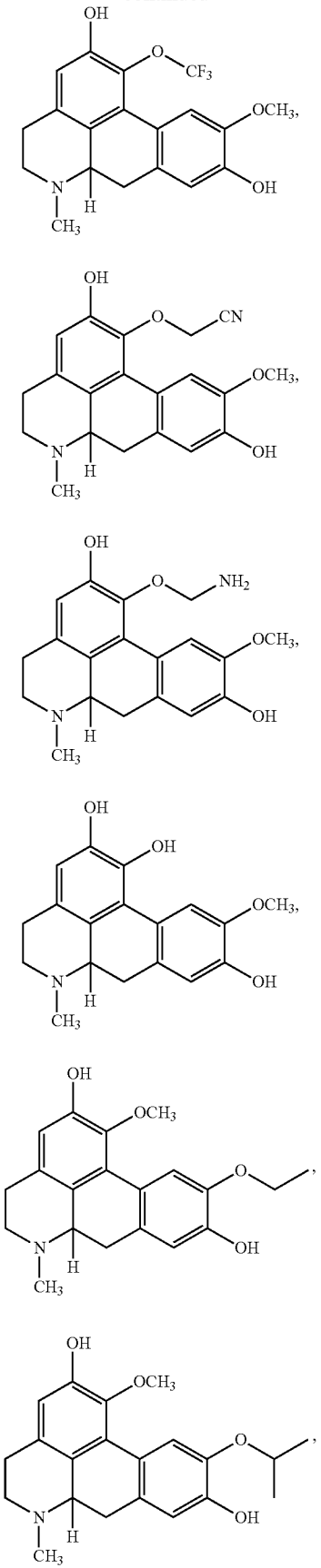

-continued
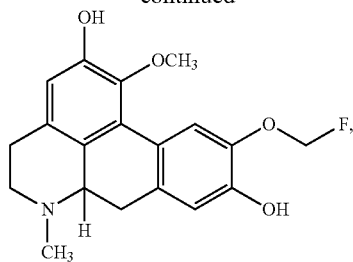
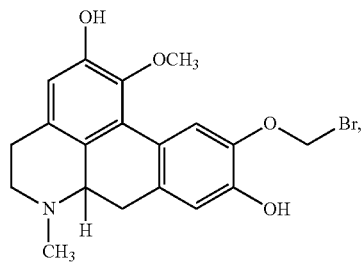
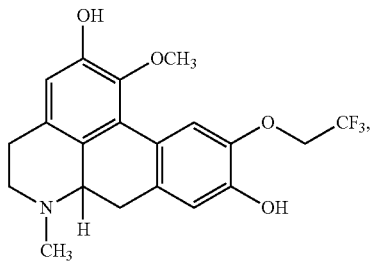
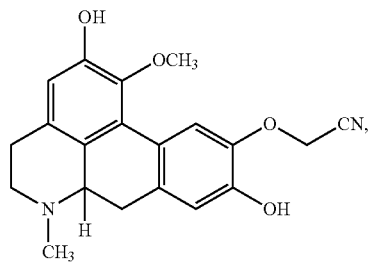
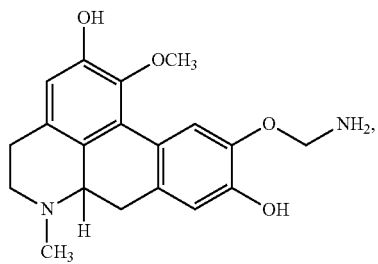
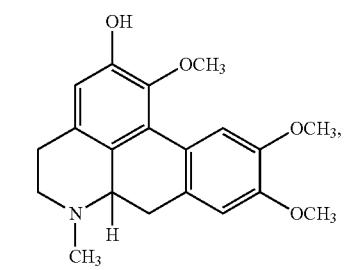
-continued
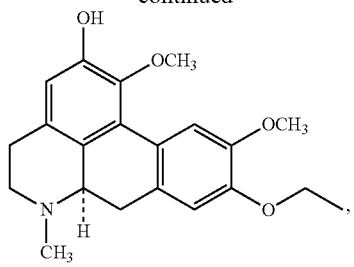
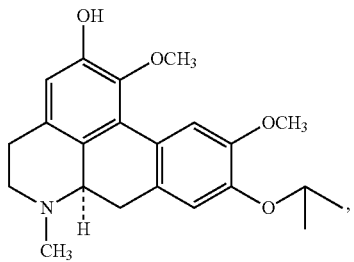
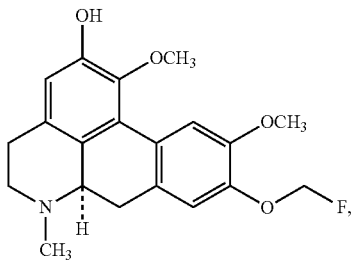
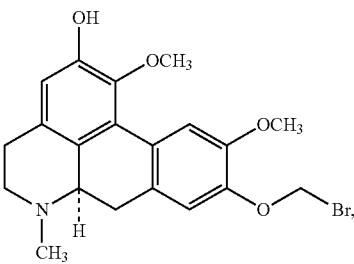
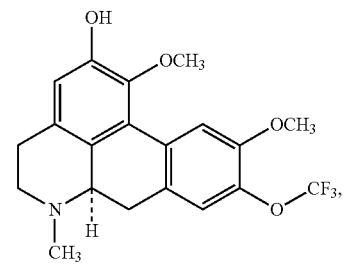
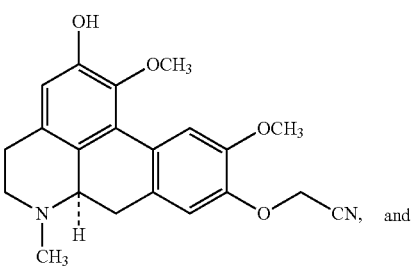

-continued

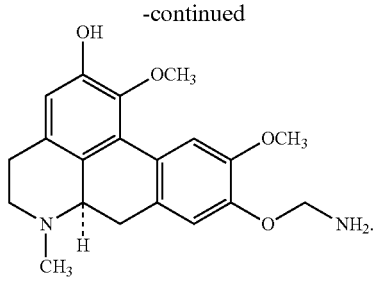

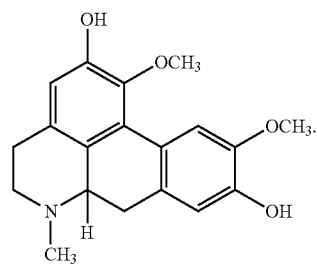 [SMILES: COc1cc2c(cc1O)CC1c3c(cc(O)c(OC)c3-2)CCN1C]

The compound shown above is the S enantiomer of boldine (also known by the IUPAC name, (S)-1,10-dimethoxy-6-methyl-5,6,6a,7-tetrahydro-4H-dibenzo[de,g]quinoline-2,9-diol). S-boldine, when present, can be substantially free of other isomers (e.g., as a pure or substantially pure optical isomer having a specified activity), or may be admixed, for example, with racemates or other stereoisomers. In one aspect, S-boldine, when present, can be about 80% enantiomerically pure, about 85% enantiomerically pure, about 90% enantiomerically pure, about 91% enantiomerically pure, about 92% enantiomerically pure, about 93% enantiomerically pure, about 94% enantiomerically pure, about 95% enantiomerically pure, about 96% enantiomerically pure, about 97% enantiomerically pure, about 98% enantiomerically pure, about 99% enantiomerically pure, or about 100% enantiomerically pure.

According to one aspect, the compound administered to the subject to treat an injury to the nervous system is represented by the formula:

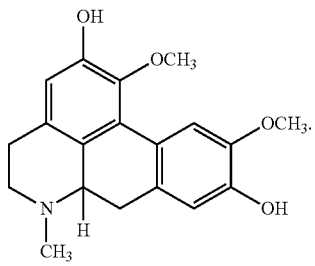 [SMILES: COc1cc2c(cc1O)CC1c3c(cc(O)c(OC)c3-2)CCN1C]

The compound shown above corresponds to a racemic mixture of boldine. Boldine is a naturally-occurring alkaloid present in the leaves and bark of Boldo (*Peumus boldus* Molina), a tree native to the central region of Chile, among other plants.

In various aspects, the compounds administered to the subject have at least one chiral center and can be substantially free of other isomers (e.g., as a pure or substantially pure optical isomer having a specified activity), or may be admixed, for example, with racemates or other stereoisomers. In one aspect, the compound can be substantially enantiomerically pure. For example, the S enantiomer of boldine can be substantially free of or separated from the R enantiomer of boldine. Similarly, for example, the R enantiomer of boldine can be substantially free of or separated from the S enantiomer of boldine. In one aspect, the compound can be about 80% enantiomerically pure, about 85% enantiomerically pure, about 90% enantiomerically pure, about 91% enantiomerically pure, about 92% enantiomerically pure, about 93% enantiomerically pure, about 94% enantiomerically pure, about 95% enantiomerically pure, about 96% enantiomerically pure, about 97% enantiomerically pure, about 98% enantiomerically pure, about 99% enantiomerically pure, or about 100% enantiomerically pure.

In one exemplary aspect, the compound administered to the subject to treat an injury to the nervous system is represented by the following formula:

In a further aspect, the method comprises improving voluntary muscle control in a subject having an injury to the nervous system, comprising administering to the subject an effective amount of a compound represented by the following formula:

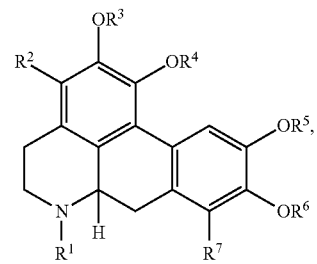

wherein $R^1$ is selected from hydrogen and C1-C4 alkyl; wherein $R^2$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^3$ and $R^4$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^3$ and $R^4$ join together to form a ring having 5-7 atoms; wherein each of $R^5$ and $R^6$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^5$ and $R^6$ join together to form a ring having 5-7 atoms; and wherein $R^7$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or a pharmaceutically-acceptable salt thereof.

In a further aspect, the method comprises improving voluntary muscle control in a subject having an injury to the nervous system, comprising administering to the subject an effective amount of a compound represented by the following formula:

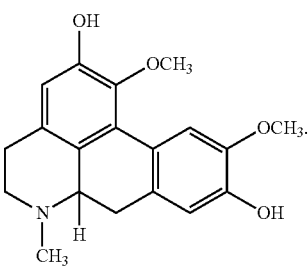 [SMILES: COc1cc2c(cc1O)CC1c3c(cc(O)c(OC)c3-2)CCN1C]

In a still further aspect, the method comprises improving voluntary muscle control in a subject having an injury to the nervous system, comprising administering to the subject an effective amount of S-boldine (or a pharmaceutically-acceptable salt thereof), which corresponds to the following structural formula:

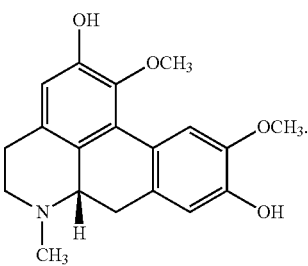

In one aspect, the method comprises treating neuropathic pain in a subject having an injury to the nervous system, comprising administering to the subject an effective amount of a compound represented by the formula:

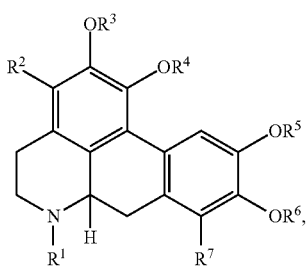

wherein $R^1$ is selected from hydrogen and C1-C4 alkyl; wherein $R^2$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^3$ and $R^4$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^3$ and $R^4$ join together to form a ring having 5-7 atoms; wherein each of $R^5$ and $R^6$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^5$ and $R^6$ join together to form a ring having 5-7 atoms; and wherein $R^7$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or a pharmaceutically-acceptable salt thereof.

In a further aspect, the method comprises treating neuropathic pain in a subject having an injury to the nervous system, comprising administering to the subject an effective amount of a compound represented by the formula:

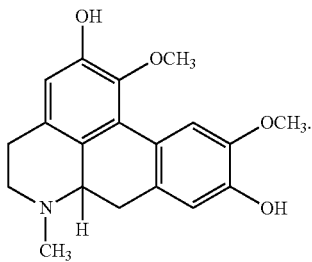 [SMILES: COc1cc2c(cc1O)CC1c3c(cc(O)c(OC)c3-2)CCN1C]

In a still further aspect, the method comprises treating neuropathic pain in a subject having an injury to the nervous system, comprising administering to the subject an effective amount of S-boldine (or a pharmaceutically-acceptable salt thereof), which corresponds to the following structural formula:

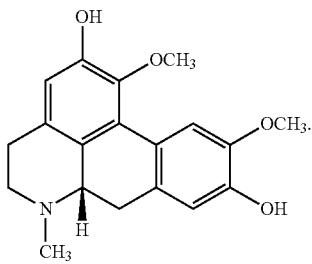

The compounds and pharmaceutically acceptable salts thereof can be administered to the subject having an injury to the nervous system via a variety of routes. Non-limiting examples include oral administration (e.g., as a tablet, capsule, lozenge, or troche) or intravenous administration of the compound together with a pharmaceutically-acceptable carrier.

The effective amount or dosage of the composition or an ingredient thereof can vary within wide limits. Such a dosage is adjusted to the individual requirements in each particular case including the specific composition(s) being administered and the condition being treated, as well as the subject being treated. In general, single dose compositions can contain such amounts or submultiples thereof of the composition to make up the daily dose. The dosage can be adjusted by the individual physician in the event of any contraindications. Dosage can vary, and can be administered in one or more dose administrations daily, for one or several days. In some aspects, the effective amount is a therapeutically effective amount. In a further aspect, the effective amount is a prophylactically effective amount.

In one aspect, the compounds can be administered to the subject having an injury to the nervous system in an amount ranging from about 1 mg/kg body weight to about 500 mg/kg body weight, using a 75 kg human as the subject. Dosages can be adjusted accordingly depending on the body weight of the subject. In a further aspect, the compounds can be administered to the subject having a nerve injury (e.g., peripheral nerve injury, spinal cord injury (SCI), or spinal cord contusion) in an amount ranging from about 1 mg/kg body weight to about 200 mg/kg body weight, using a 75 kg human as the subject.

In a further aspect, the compounds can be administered to the subject having a nerve injury (e.g., peripheral nerve injury, spinal cord injury (SCI), or spinal cord contusion) in an amount ranging from about 1 mg/kg body weight to about 100 mg/kg body weight, using a 75 kg human as the subject. In a further aspect, the compounds can be administered to the subject having a nerve injury (e.g., peripheral nerve injury, spinal cord injury (SCI), or spinal cord contusion) in an amount ranging from about 1 mg/kg body weight to about 50 mg/kg body weight, using a 75 kg human as the subject. In a further aspect, the compounds can be administered to the subject having a nerve injury (e.g., peripheral nerve injury, spinal cord injury (SCI), or spinal cord contusion) in an amount ranging from about 1 mg/kg body weight to about 25 mg/kg body weight, using a 75 kg human as the subject. In a further aspect, the compounds can be administered to the subject having a nerve injury (e.g., peripheral nerve injury, spinal cord injury (SCI), or spinal cord contusion) in an amount ranging from about 1 mg/kg body weight to about 10 mg/kg body weight, using a 75 kg human as the subject.

In a further aspect, the compounds can be administered to the subject having a nerve injury (e.g., peripheral nerve injury, spinal cord injury (SCI), or spinal cord contusion) in an amount ranging from about 1 mg/kg body weight to about 5 mg/kg body weight, using a 75 kg human as the subject. In a further aspect, the compounds can be administered to the subject having a nerve injury (e.g., peripheral nerve injury, spinal cord injury (SCI), or spinal cord contusion) in an amount ranging from about 1 mg/kg body weight to about 4 mg/kg body weight, using a 75 kg human as the subject.

In one aspect, when the subject suffers from an injury to the nervous system such as a spinal cord injury (SCI) or spinal cord contusion, the compounds can be administered to the subject via intravenous administration up to 24 hours after the injury to the nervous system. In a further aspect, the compounds can be administered to the subject over a longer period of time, e.g., days, months, or years, for example through an oral dosage form.

In one aspect, the subject to be treated is a mammal. In a further aspect, the subject is a human. In a still further aspect, the subject has been diagnosed with a need for treatment of an injury to the nervous system prior to the administering step. In a further aspect, the treatment method comprises the step of identifying a subject in need of treatment of an injury to the nervous system prior to the administering step.

In one aspect, the subject to be treated suffers from neuropathic pain. Neuropathic pain is often seen in several cases of nervous system injuries, including without limitation spinal cord injury (SCI) or spinal cord contusion. In the spinal cord, the spinal thalamic tract (STT) constitutes the major ascending nociceptive pathway. As a result of sustained spontaneous activity occurring in the periphery, STT neurons in the dorsal horn improve increased response to afferent impulses, including increased background activity, enlarged receptive fields, and normally harmless tactile stimuli. This phenomenon is called central sensitization. Central sensitization can be an important mechanism of persistent neuropathic pain. Non-neuronal glial cells and immune responses play a role in central sensitization.

A typical symptom of neuropathic pain is sensory abnormalities (often spontaneous or induced burning pain associated with superimposed lightning components), but pain can be deep and tingling. Other sensations can occur, such as hypersensitivity, hyperalgesia, allodynia (pain from non-noxious stimuli), and hyperalgesia (especially unpleasant, excessive pain response). As the CNS is sensitized and remodeled, the symptoms persist and generally persist after the main cause of the symptoms (if one is present) is resolved.

Peripheral nerve injuries also causes reactions in peripheral immune cells and glia at several different anatomical sites. The response is that macrophages and Schwann cells promote the Wallerian degeneration of axotomized nerve fibers distal to the nerve lesion, the immune responses in dorsal root ganglia (DRGs), and macrophages and lymphocytes driven by satellite cells. Spinal microglial activation dominates the CNS early glial response to peripheral nerve injury followed by astrocyte activation and proliferation.

In various aspects, the neuropathic chronic pain that can be treated using the disclosed compounds can be, for example, pain that lasts for a long period of at least one month or longer. As discussed above, the pain can be a result of traumatic injury to the nervous system, such as a spinal cord injury (SCI) or spinal cord contusion or other injury to the nervous system resulting from trauma instead of disease.

In a further aspect, the compounds can be administered to the subject having an injury to the nervous system to improve voluntary muscle control of the subject. In one aspect, the compounds can be administered to the subject having an injury to the nervous system to improve locomotor function in the subject. Following administration of boldine or its analogs, locomotor function can be evaluated using methods known in the art, including those described below in Section E.1.

C. Manufacture of a Medicament

In one aspect, disclosed is the use of a compound having the following formula in the manufacture of a medicament for the treatment of an injury to the nervous system:

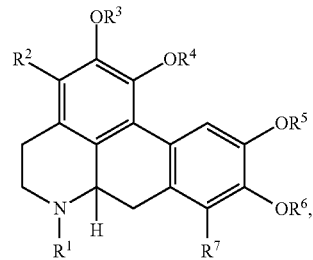

wherein $R^1$ is selected from hydrogen and C1-C4 alkyl; wherein $R^2$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^3$ and $R^4$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^3$ and $R^4$ join together to form a ring having 5-7 atoms; wherein each of $R^5$ and $R^6$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^5$ and $R^6$ join together to form a ring having 5-7 atoms; and wherein $R^7$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or a pharmaceutically-acceptable salt thereof.

In a further aspect, disclosed is the use of a compound having the following formula, or a pharmaceutically-acceptable salt thereof, in the manufacture of a medicament for the treatment of an injury to the nervous system:

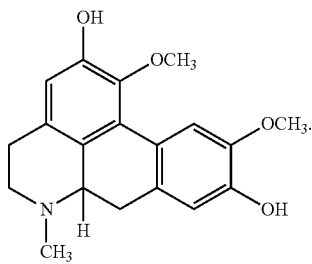 [SMILES: COc1cc2c(cc1O)CC1c3c(cc(O)c(OC)c3-2)CCN1C]

In a still further aspect, disclosed is the use of a compound having the following formula, or a pharmaceutically-acceptable salt thereof, in the manufacture of a medicament for the treatment of an injury to the nervous system:

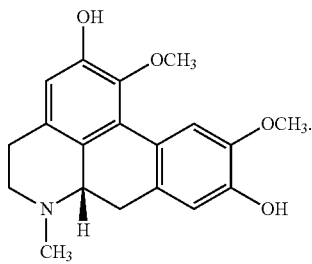

In yet a further aspect, disclosed is the use of a pharmaceutically-acceptable salt of S-boldine, e.g., S-boldine hydrochloride or another suitable salt as described above, in the manufacture of a medicament for the treatment of an injury to the nervous system in a subject.

In various aspects, the method for the manufacture of a medicament comprises combining a therapeutically effective amount of a disclosed compound with a pharmaceutically acceptable carrier or diluent. In a further aspect, disclosed is a method for the manufacture of a medicament for treating an injury to the nervous system in a subject, the method comprising combining a therapeutically effective amount of a disclosed compound with a pharmaceutically acceptable carrier or diluent.

According to one aspect, the injury to the nervous system is a central nervous system injury or a peripheral nervous system injury. In a further aspect, the injury to the nervous system is a spinal cord injury (SCI), spinal cord contusion, nerve crush injury, or traumatic brain injury (TBI). In a still further aspect, a symptom of the injury to the nervous system is neuropathic pain, loss of voluntary muscle control, loss of locomotor function, or a combination thereof.

D. Kits

In a further aspect, disclosed is a kit comprising a compound having the following formula and instructions for the use thereof for the treatment of an injury to the nervous system in a subject:

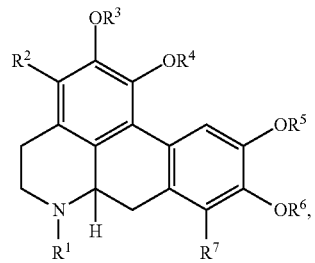

wherein $R^1$ is selected from hydrogen and C1-C4 alkyl; wherein $R^2$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; wherein each of $R^3$ and $R^4$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^3$ and $R^4$ join together to form a ring having 5-7 atoms; wherein each of $R^5$ and $R^6$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^5$ and $R^6$ join together to form a ring having 5-7 atoms; and wherein $R^7$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or a pharmaceutically-acceptable salt thereof.

In another aspect, disclosed is a kit comprising a compound having the following formula, or a pharmaceutically-acceptable salt thereof, and instructions for the use thereof for the treatment of an injury to the nervous system in a subject:

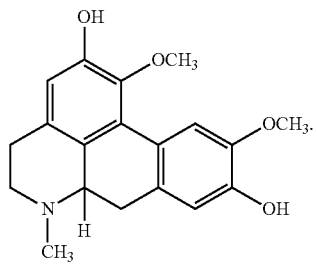

In another aspect, disclosed is a kit comprising a compound having the following formula, or a pharmaceutically-acceptable salt thereof, and instructions for the use thereof for the treatment of an injury to the nervous system in a subject:

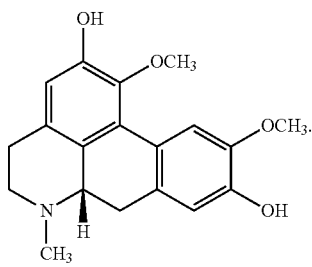

In yet a further aspect, disclosed is a kit comprising a pharmaceutically-acceptable salt of S-boldine, e.g., S-boldine hydrochloride or another suitable salt as described above, and instructions for the use thereof for the treatment of an injury to the nervous system in a subject.

In various aspects, the compounds or a pharmaceutically-acceptable salt thereof, and the instructions for the use thereof for the treatment of an injury to the nervous system can be co-packaged. In a still further aspect, the compound or pharmaceutically-acceptable salt thereof and the instructions are not co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds and pharmaceutical formulations. It is also understood that the disclosed kits can be employed in connection with the disclosed methods of using the compounds and pharmaceutical formulations.

According to one aspect, the injury to the nervous system is a central nervous system injury or a peripheral nervous system injury. In a further aspect, the injury to the nervous system is a spinal cord injury (SCI), spinal cord contusion, nerve crush injury, or traumatic brain injury (TBI). In a still further aspect, a symptom of the injury to the nervous system is neuropathic pain, loss of voluntary muscle control, loss of locomotor function, or a combination thereof.

E. Examples

The following examples are put forth so as to provide those of ordinary skill in the art with a complete disclosure and description of how the methods and products claimed herein are made and evaluated, and are intended to be purely exemplary and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric. The Examples are provided herein to illustrate the invention, and should not be construed as limiting the invention in any way.

1. Functional Recovery after Boldine Treatment

Figure 1C:
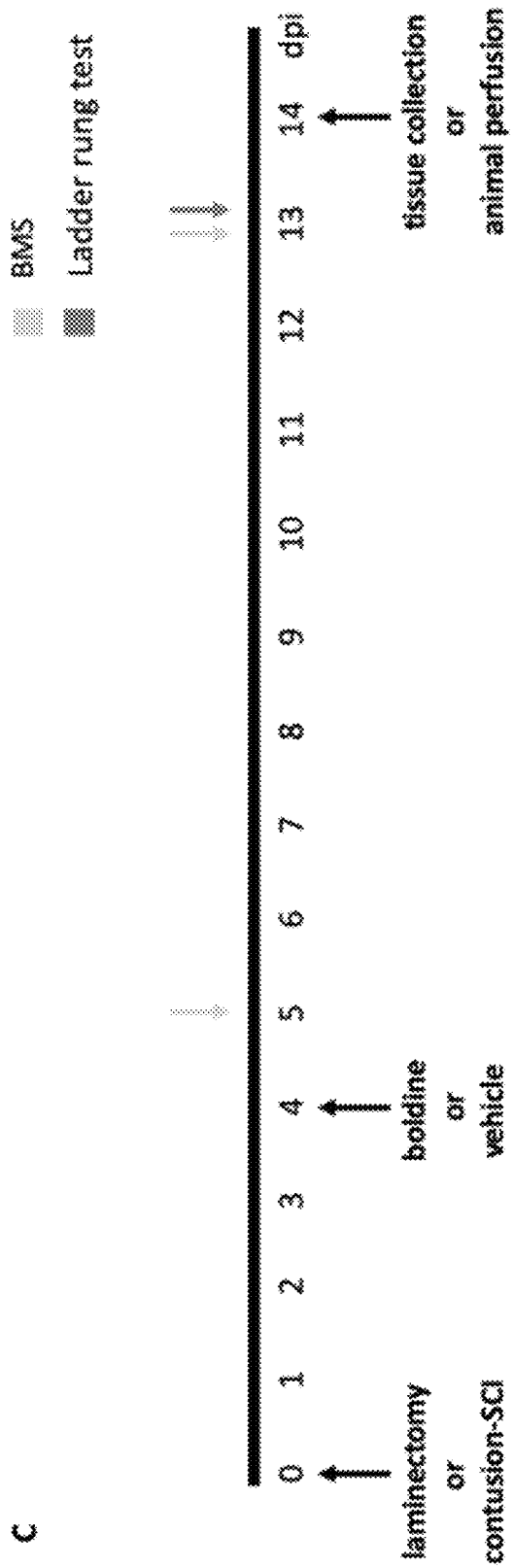

With references to FIGS. 1A-C, oral administration of boldine to 3-month old C57BL6 mice that have undergone a moderate contusion spinal cord injury (SCI), achieved after a 50 kdyn impact contusion at T9-T10, significantly improves locomotor function. Function was determined by behavioral testing using both the Basso Mouse Scale (BMS) score (FIG. 1A) and the ladder rung walk test (LRWT) (FIG. 1B). A timeline for these studies is shown in FIG. 1C. While sham mice had normal BMS scores a few days after laminectomy, the BMS scores for contusion-SCI mice were much lower. Twice daily boldine treatment starting at 4-dpi significantly increased BMS scores at 13 dpi (FIG. 1A). Analysis of LRWT done at 13-dpi showed that boldine-treated mice had many fewer incorrect steps (13%) than vehicle-treated SCI mice (83%) (FIG. 1B). (N=5; ANOVA *p<0.05 and **p<0.005 respectively).

Figure 2A:
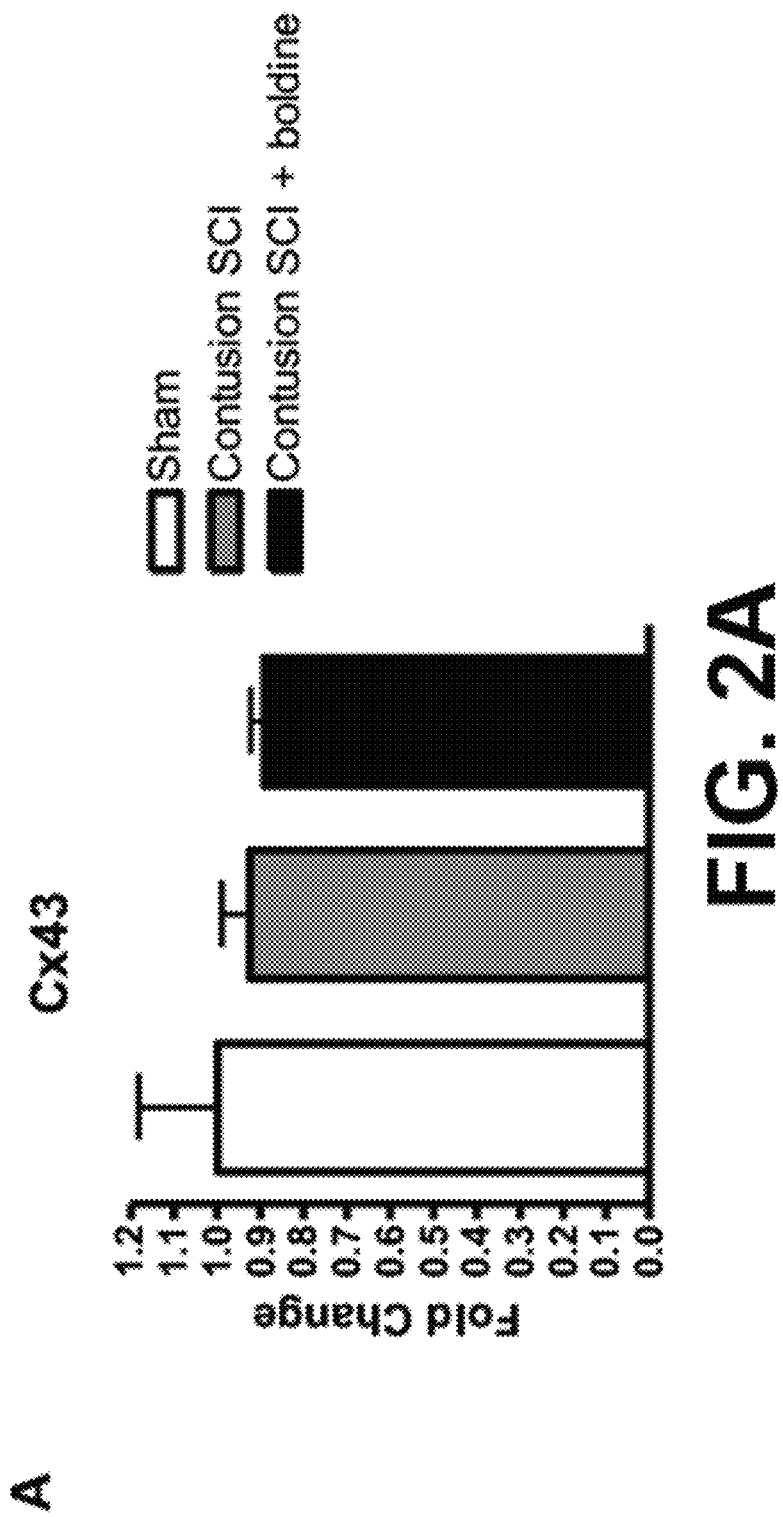
Figure 2B:
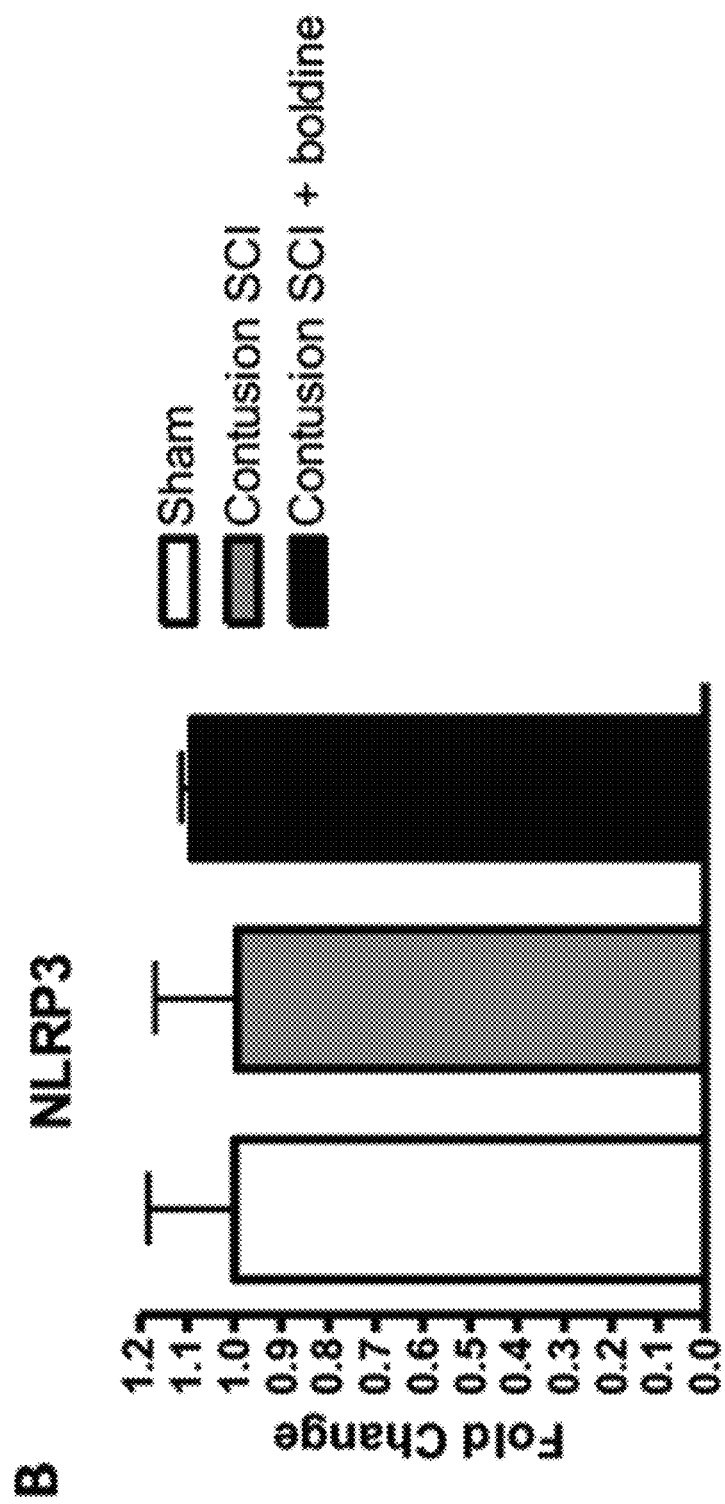
Figure 2D:
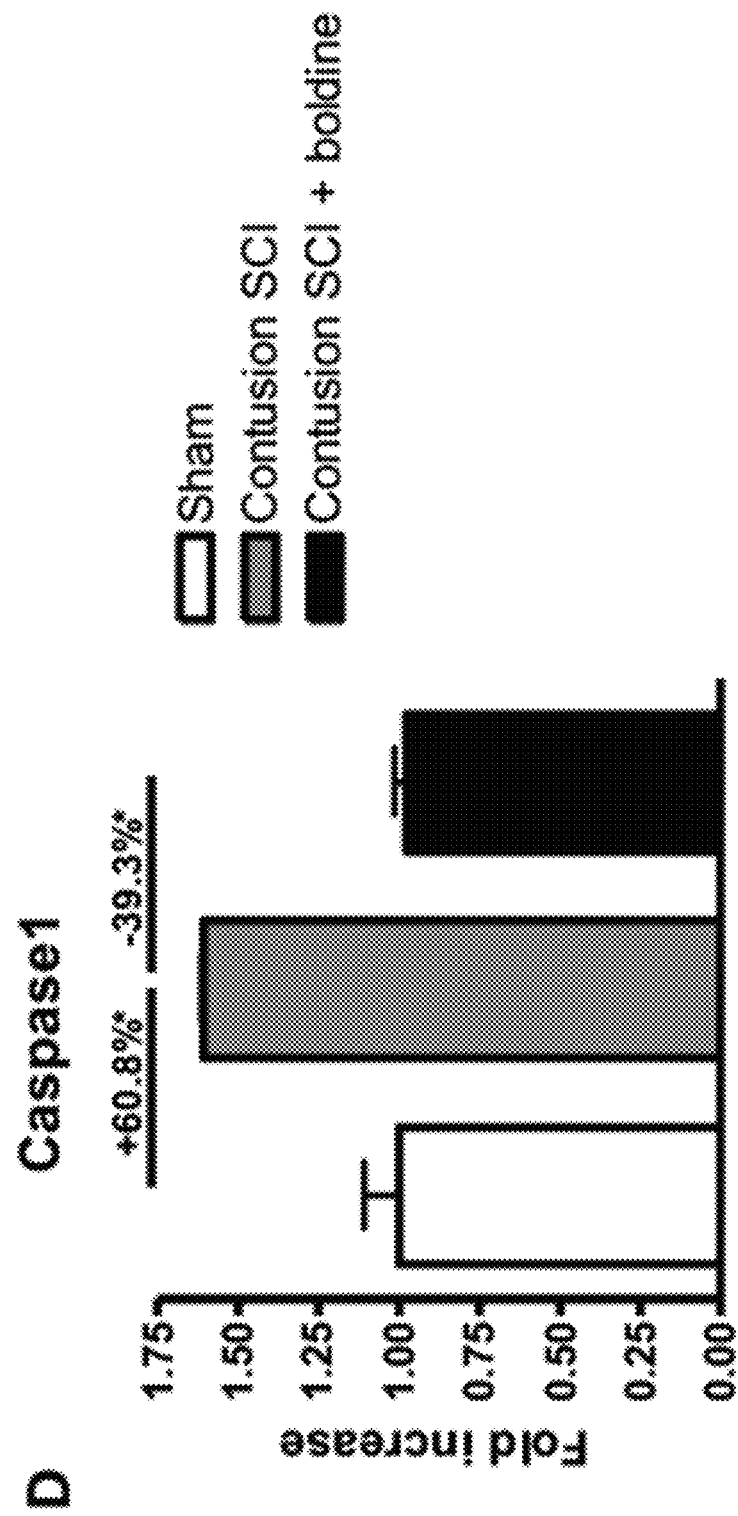
Figure 3A:
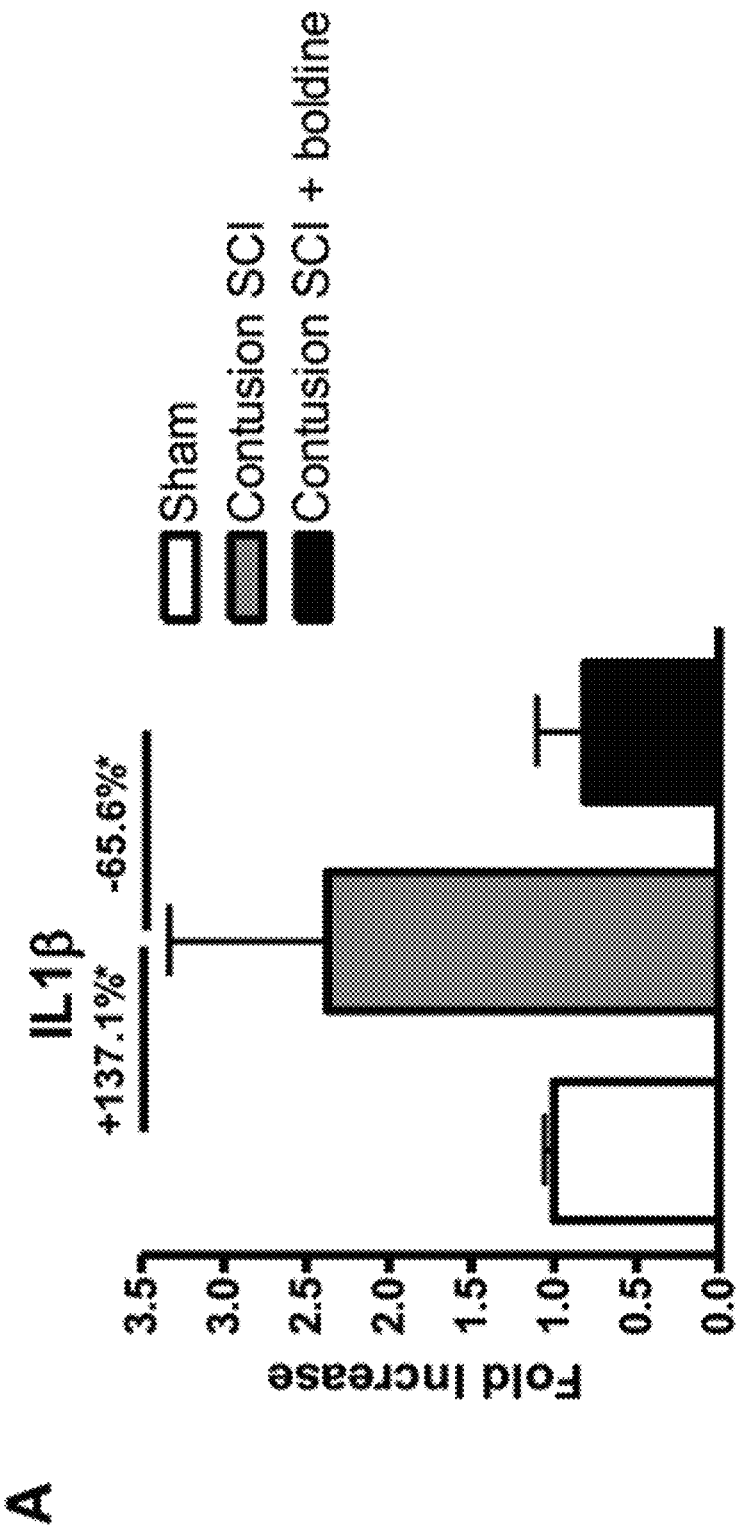

2. Reduction in Hippocampal mRNA Levels for Caspase-1 and IL-1β after Sci Following Boldine Treatment In rats, a spinal cord injury (SCI) can result in cognitive deficits that are associated with activation in brain regions linked to pain processing and cognition of microglia and astrocytes as well as associated with upregulation of a gene involved in inflammation (Wu et al. 2013; Wu et al. 2014). Such changes may drive central pain in neuropathic pain syndromes. To determine whether boldine mitigates such changes, mRNA expression of Cx43 and genes involved in inflammasome assembly and activity were determined in mouse brains. While SCI increased caspase-1 in the hippocampus. This change appeared to be corrected by boldine (FIG. 2). Similarly, boldine significantly reduced mRNA levels of IL-10 by 65.5%, and CCL2 in 47.2% when compared to mRNA levels of vehicle-treated animals after contusion SCI (N=3, * p<0.05 by one-way ANOVA) (FIG. 3). These studies indicate that boldine can reduce neuropathic pain following spinal cord injury (SCI) associated with reductions in brain and spinal cord of expression of pro-inflammatory cytokines and chemokines linked to pathological pain.

3. RNA Sequence Analysis

Additional studies were performed using tissues harvested from the mice for which behavioral testing data showing effects of boldine on Basso Mouse Scale and ladder rung walk test were collected. RNA-seq analysis was performed on spinal cord segments from SCI mice at 14-dpi treated with boldine or vehicle starting at 4-dpi (N=3 for each). Differentially expressed genes (DEGs) were clustered by their gene ontology (GO) and enrichment of GO terms was tested using a Fisher's exact test (GeneSCF v1.1-p2). Enriched DEGs were involved in pathways related to neutrophil activation and aggregation, inflammatory responses and astrocyte development.

Genes from a list of the top DEGs from the RNA-seq analysis were considered and tested for differences in gene expression of pro-inflammatory chemokines Ccl2 and Ccl3 between vehicle and boldine treated spinal cord tissues from C57B6 SCI animals at 14-dpi. Laminectomy-only (Sham) animals as were used as controls. Levels of both chemokines were significantly increased at 14-dpi in SCI vehicle-treated animals compared to shams (N=3 ANOVA *p<0.05). Boldine resulted in an apparent decrease which did not reach our threshold for significance (N=3 ANOVA p=0.091 and p=0.085, respectively). These results are consistent with the bulk RNA-seq data.

4. Immunofluorescence Staining Studies

Immunofluorescence staining was performed on injured spinal cords of vehicle and boldine treated SCI mice at 14-dpi. 30-micron transverse sections were used to evaluate differences in the labeling of the neurite outgrowth marker GAP-43. GAP43 immunofluorescence was dramatically increased in sections from boldine treated compared to vehicle animals.

5. Reduction of mRNA Levels of CCL2

To model effects of boldine on release of chemokines and other mediators, changes in mRNA expression after lipopolysaccharide (LPS)-induced inflammatory responses were analyzed using astrocytic primary cell cultures. These studies show that boldine treatment of LPS astrocytes significantly reduces mRNA levels of CCL2 by 38% compared to mRNA levels of vehicle-treated LPS astrocytes.

It will be apparent to those skilled in the art that various modifications and variations can be made without departing from the scope or spirit of this disclosure. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method of improving voluntary muscle control in a subject having an injury to the nervous system, comprising administering to the subject an effective amount of a compound represented by the formula:

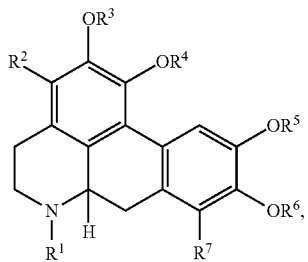

wherein $R^1$ is selected from hydrogen and C1-C4 alkyl;
wherein $R^2$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;
wherein each of $R^3$ and $R^4$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^3$ and $R^4$ join together to form a ring having 5-7 atoms;
wherein each of $R^5$ and $R^6$ is independently selected from hydrogen, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl; or wherein $R^5$ and $R^6$ join together to form a ring having 5-7 atoms; and
wherein $R^7$ is selected from hydrogen, halogen, —CN, —NH$_2$, —OH, —NO$_2$, C1-C4 alkyl, C2-C4 alkenyl, C1-C4 haloalkyl, C1-C4 cyanoalkyl, C1-C4 hydroxyalkyl, C1-C4 haloalkoxy, C1-C4 alkoxy, C1-C4 alkylamino, (C1-C4)(C1-C4) dialkylamino, and C1-C4 aminoalkyl;
or a pharmaceutically acceptable salt thereof, thereby improving voluntary muscle control in the subject.

2. The method of claim 1, wherein each of $R^1$, $R^4$, and $R^5$ is independently selected from hydrogen, methyl, ethyl, and propyl; wherein each of $R^2$ and $R^7$ is independently selected from hydrogen and halogen; and wherein each of $R^3$ and $R^6$ is hydrogen.

3. The method of claim 1, wherein each of $R^1$, $R^4$, and $R^5$ is methyl; wherein each of $R^2$ and $R^7$ is independently selected from hydrogen and halogen; and wherein each of $R^3$ and $R^6$ is hydrogen.

4. The method of claim 1, wherein each of $R^1$, $R^4$, and $R^5$ is independently selected from hydrogen, methyl, ethyl, and propyl; and wherein each of $R^2$, $R^3$, $R^6$, and $R^7$ is hydrogen.

5. The method of claim 1, wherein the compound is represented by the formula:

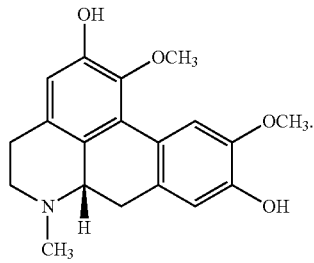

6. The method of claim 1, wherein the injury to the nervous system is a spinal cord injury (SCI), spinal cord contusion, nerve crush injury, or traumatic brain injury (TBI).

7. The method of claim 1, wherein a symptom of the injury to the nervous system is neuropathic pain.

8. The method of claim 1, wherein improving voluntary muscle control comprises improving locomotor function.

* * * * *